(12) United States Patent
Dezawa

(10) Patent No.: US 11,920,180 B2
(45) Date of Patent: Mar. 5, 2024

(54) METHOD FOR INDUCING DIFFERENTIATION OF PLURIPOTENT STEM CELLS IN VITRO

(71) Applicant: TOHOKU UNIVERSITY, Sendai (JP)

(72) Inventor: Mari Dezawa, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 873 days.

(21) Appl. No.: 16/322,746

(22) PCT Filed: Aug. 3, 2017

(86) PCT No.: PCT/JP2017/028327
§ 371 (c)(1),
(2) Date: Feb. 1, 2019

(87) PCT Pub. No.: WO2018/025975
PCT Pub. Date: Feb. 8, 2018

(65) Prior Publication Data
US 2019/0185903 A1 Jun. 20, 2019

(30) Foreign Application Priority Data
Aug. 3, 2016 (JP) ................. 2016-153259

(51) Int. Cl.
*C12Q 1/04* (2006.01)
*C12N 5/074* (2010.01)
*C12N 5/07* (2010.01)
*C12N 5/0735* (2010.01)
*C12N 15/09* (2006.01)

(52) U.S. Cl.
CPC .............. *C12Q 1/04* (2013.01); *C12N 5/06* (2013.01); *C12N 5/0606* (2013.01); *C12N 5/0696* (2013.01); *C12N 15/09* (2013.01); *C12N 2502/08* (2013.01); *C12N 2502/1329* (2013.01); *C12N 2506/45* (2013.01)

(58) Field of Classification Search
CPC ............................ C12N 5/0607; C12N 5/0696
See application file for complete search history.

(56) References Cited

U.S. PATENT DOCUMENTS

| | | |
|---|---|---|
| 2004/0235165 A1 | 11/2004 | Prockop et al. |
| 2011/0070205 A1 | 3/2011 | Crawford et al. |
| 2011/0070647 A1 | 3/2011 | Dezawa et al. |
| 2011/0274664 A1 | 11/2011 | Harn et al. |
| 2012/0122214 A1 | 5/2012 | Senju |
| 2015/0196600 A1 | 7/2015 | Yoshida et al. |

FOREIGN PATENT DOCUMENTS

| | | |
|---|---|---|
| JP | 2010-268789 A | 12/2010 |
| WO | WO 2011/007900 A1 | 1/2011 |

OTHER PUBLICATIONS

Rollin, 2004, Molecular Vision, 10:15-22.*
Ketola, 2010, J Clin Endocrinol Metab, 85:3925-3931.*
Abu-Hassan (Stem Cells 2015;33:751-761).*
Wakao (2022, Cellular and Molecular Life Sciences, 79:542).*
Mohsin, S., et al., "Enhanced hepatic differentiation of mesenchymal stem cells after pretreatment with injured liver tissue", Differentiation, vol. 81, Jan. 1, 2011, pp. 42-48.
Iseki, M., et al., "Human Muse Cells, Nontumorigenic Pluripotent-Like Stem Cells, Have Liver Regeneration Capacity Through Specific Homing and Cell Replacement in a Mouse Model of Liver Fibrosis", Cell Transplantation, vol. 26. May 1, 2017, pp. 821-840.
Kuroda, Y., et al., "Unique multipotent cells in adult human mesenchymal cell populations", PNAS, vol. 107, No. 19, Apr. 26, 2010, pp. 8639-8643, 2010.
Dezawa, M., "Muse Cells Provide the Pluripotency of Mesenchymal Stem Cells:, Direct Contribution of Muse Cells to Tissue Regeneration", Cell Transplantation, 2016, vol. 25, pp. 849-861.
International Search Report dated Oct. 31, 2017 in PCT/JP2017/028327 (with English translation), 4 pages.
Gloria Hoi Wan Tso, et al., "Phagocytosis oproptotic Cells Modulates Mesenchymal Stem Cells Osteogenic Differentiation to Enhance IL-17 and RANKL Expression on CD4+ T Cells" Stem Cells, vol. 28, 2010, pp. 939-954.
Spees, J.L. et al, "Differentiation, cell fusion, and nuclear fusion during ex vivo repair of epithelium by human adult stem cells from bone marrow stroma", Proc. Natl. Acad. Sci., USA, 2003, 100(5): pp. 2397-2402 (Mar. 4, 2003).
Prockop, D.J., et al, "One strategy for cell and gene therapy: Harnessing the power of adult stem cells to repair tissues", Proc. Natl. Acad. Sci., USA. 2003, 100 (Suppl 1): pp. 11917-11923, (Sep. 30, 2003).
Strassburg, S., et al, "Co-culture induces mesenchymal stem cell differentiation and modulation of the degenerate human nucleus pulposus cell phenotype", Regenerative Medicine, 2010, 5(5): pp. 701-711 (Sep. 2010).
Strassburg, S., et al, "Bi-Directional Exchange of Membrane Components Occurs during Co-Culture of Mesenchymal Stem Cells and Nucleus Pulposus Cells", PLoS One, 2012, 7(3) :e33739 (9 total pages). (Mar. 2012).
Wakao, S., et al, "Phagocytosing differentiated cell-fragments is a novel mechanism for controlling somatic stem cell differentiation within a short time frame", Cellular and Molecular Life Sciences, 2022, 79(11): p. 542 (35 total pages), (Oct. 6, 2022).

\* cited by examiner

*Primary Examiner* — Valarie E Bertoglio
(74) *Attorney, Agent, or Firm* — Oblon, McClelland, Maier & Neustadt, L.L.P.

(57) ABSTRACT

The purpose of the present invention is to provide a cell creation method that enables a reduction in cost and time, that is highly safe, and that has great potential for being industrially applied. Provided by the present invention is a method for inducing differentiation of pluripotent cells in vitro into cells having a same phenotype and function as information-presentation cells, the method comprising co-culturing pluripotent cells or a cellular fraction having said pluripotent cells concentrated therein, together with damaged cells or dead cells derived from information-presentation cells, or together with a portion of the damaged cells or dead cells derived from information-presentation cells.

17 Claims, 9 Drawing Sheets

Specification includes a Sequence Listing.

SEQUENCE LISTING

```
<160> NUMBER OF SEQ ID NOS: 27

<210> SEQ ID NO 1
<211> LENGTH: 1669
<212> TYPE: DNA
<213> ORGANISM: Homo sapiens

<400> SEQUENCE: 1
gctcctgtca tcgaggcccc tggcccaatg gcaggctgag tcccctcct  ctggcctggt    60 cccgcctctc ctgccccttg tgctcagcgc tacctgctgc ccggacacat ccagagctgg   120
ccgacgggtg cgcgggcggg cggcggcacc atgcaggaa  gctgccaggg gccgtgggca   180
gcgccgcttt ctgccgccca cctggcgctg tgagactggc gctgccacca tgttccccag   240
ccctgctctc acgcccacgc ccttctcagt caaagacatc ctaaacctgg aacagcagca   300
gcgcagcctg gctgccgccg gagagctctc tgcccgcctg gaggcgaccc tggcgccctc   360
ctcctgcatg ctggccgcct tcaagccaga ggcctacgct gggcccgagg cggctgcgcc   420
gggcctccca gagctgcgcg cagagctggg ccgcgcgcct tcaccggcca agtgtgcgtc   480
tgcctttccc gccgcccccg ccttctatcc acgtgcctac agcgaccccg acccagccaa   540
ggaccctaga gccgaaaaga aagagctgtg cgcgctgcag aaggcggtgg agctggagaa   600
gacagaggcg gacaacgcgg agcggccccg ggcgcgacgg cggaggaagc cgcgcgtgct   660
cttctcgcag gcgcaggtct atgagctgga gcggcgcttc aagcagcagc ggtacctgtc   720
ggcccccgaa cgcgaccagc tggccagcgt gctgaaactc acgtccacgc aggtcaagat   780
ctggttccag aaccggcgct acaagtgcaa gcggcagcgg caggaccaga ctctggagct   840
ggtggggctg ccccgccgc cgccgccgcc tgcccgcagg atcgcggtgc cagtgctggt   900
gcgcgatggc aagccatgcc tagggactc ggcgccctac gcgcctgcct acggcgtggg   960
cctcaatccc tacggttata acgcctaccc cgcctatccg ggttacggcg gcgcggcctg  1020
cagccctggc tacagctgca ctgccgctta ccccgccggg ccttccccag cgcagccggc  1080
cactgccgcc gccaacaaca acttcgtgaa cttcggcgtc ggggacttga atgcggttca  1140
```

-continued

```
gagccccggg attccgcaga gcaactcggg agtgtccacg ctgcatggta tccgagcctg    1200
gtagggaagg gacccgcgtg gcgcgaccct gaccgatccc acctcaacag ctccctgact    1260
ctcgggggga aaggggctc ccaacatgac cctgagtccc ctggattttg cattcactcc     1320
tgcggagacc taggaacttt ttctgtccca cgcgcgtttg ttcttgcgca cgggagagtt    1380
tgtggcggcg attatgcagc gtgcaatgag tgatcctgca gcctggtgtc ttagctgtcc    1440
ccccaggagt gccctccgag agtccatggg caccccggt tggaactggg actgagctcg     1500
ggcacgcagg gcctgagatc tggccgccca ttccgcgagc cagggccggg cgcccgggcc    1560
tttgctatct cgccgtcgcc cgcccacgca cccacccgta tttatgtttt tacctattgc    1620
tgtaagaaat gacgatcccc ttcccattaa agagagtgcg ttgaccccg                1669
```

<210> SEQ ID NO 2
<211> LENGTH: 21
<212> TYPE: DNA
<213> ORGANISM: Artificial Sequens
<220> FEATURE:
<223> OTHER INFORMATION: Forward primer for amplifying Nkx2.5

<400> SEQUENCE: 2

```
caggaccaga ctctggagct g                                                 21
```

<210> SEQ ID NO 3
<211> LENGTH: 21
<212> TYPE: DNA
<213> ORGANISM: Artificial Sequence
<220> FEATURE:
<221> NAME/KEY: Reverse primer for amplifying Nkx2.5

<400> SEQUENCE: 3

```
cgccgaagtt cacgaagttg t                                                 21
```

<210> SEQ ID NO 4
<211> LENGTH: 3419
<212> TYPE: DNA
<213> ORGANISM: Homo sapiens

<400> SEQUENCE: 4

```
ttggaggcgg ccggcgcagg ggccgcgaga ggcttcgtcg ccgctgcagc tccgggggct      60
cccaggggag cgtgcgcgga acctccaggc ccagcaggac cccggctgcg gcgaggagga     120
aggagccagc ctagcagctt ctgcgcctgt ggccgcgggt gtcctggagg cctctcggtg    180
tgacgagtgg gggacccgaa ggctcgtgcg ccacctccag gcctgacgc tgccctccgt      240 cttctgcccc caataggtgc gccggacctt caggccctgg ggtgaattca gctgctccta     300
catcagcttc cggaaccacc aaaaattcaa attgggattt tccggagtaa acaagagcct     360
agagcccttt gctcaatgct ggatttaata cgtatatatt tttaagcgag ttggtttttt     420
cccctttgat ttttgatctt cgcgacagtt cctcccacgc atattatcgt tgttgccgtc     480 gtttttctctc cccgcgtggc tccttgacct gcgaggagga gagaggacac cgaagccggg    540
agctcgcagg gaccatgtat cagagcttgg ccatggccgc caaccacggg ccgccccccg     600
gtgcctacga ggcgggcggc cccgcgcgcct tcatgcacgg cgcggggcgcc gcgtcctcgc    660 cagtctacgt gcccacaccg cgggtgccct cctccgtgct gggcctgtcc tacctccagg     720
gcggaggcgc gggctctgcg tccggaggcg cctcgggcgg cagctccggt ggggccgcgt      780
ctggtgcggg gccggacc cagcagggca gcccgggatg gagccaggcg ggagccgacg       840
gagccgctta caccccgccg ccggtgtcgc cgcgcttctc cttcccgggg accaccgggt     900
```

```
cccctggcggc cgccgccgcc gctgccgcgg cccgggaagc tgcggcctac agcagtggcg    960
gcggagcggc gggtgcgggc ctggcgggcc gcgagcagta cgggcgcgcc ggcttcgcgg   1020
gctcctactc cagcccctac ccggcttaca tggccgacgt gggcgcgtcc tgggccgcag   1080
ccgccgccgc ctccgccggc cccttcgaca gcccggtcct gcacagcctg cccggccggg   1140
ccaacccggc cgcccgacac cccaatctcg atatgtttga cgacttctca gaaggcagag   1200
agtgtgtcaa ctgtggggct atgtccaccc cgctctggag gcgagatggg acgggtcact   1260
atctgtgcaa cgcctgcggc ctctaccaca agatgaacgg catcaaccgg ccgctcatca   1320
agcctcagcg ccggctgtcc gcctcccgcc gagtgggcct ctcctgtgcc aactgccaga   1380
ccaccaccac cacgctgtgg cgccgcaatg cggagggcga gcctgtgtgc aatgcctgcg   1440
gcctctacat gaagctccac ggggtcccca ggcctcttgc aatgcggaaa gaggggatcc   1500
aaaccagaaa acggaagccc aagaacctga ataaatctaa gacaccagca gctccttcag   1560
gcagtgagag ccttcctccc gccagcggtg cttccagcaa ctccagcaac gccaccacca   1620
gcagcagcga ggagatgcgt cccatcaaga cggagcctgg cctgtcatct cactacgggc   1680
acagcagctc cgtgtcccag acgttctcag tcagtgcgat gtctggccat gggccctcca   1740
tccaccctgt cctctcggcc ctgaagctct ccccacaagg ctatgcgtct cccgtcagcc   1800
agtctccaca gaccagctcc aagcaggact cttggaacag cctggtcttg gccgacagtc   1860
acggggacat aatcactgcg taatcttccc tcttccctcc tcaaattcct gcacggacct   1920
gggacttgga ggatagcaaa gaaggaggcc ctgggctccc aggggccggc tcctctgcc    1980 tggtaatgac tccagaacaa caactgggaa gaaacttgaa gtcgacaatc tggttagggg   2040
aagcgggtgt tggattttct cagatgcctt tacacgctga tgggactgga gggagcccac   2100
ccttcagcac gagcacactg catctctcct gtgagttgga gacttctttc ccaagatgtc   2160
cttgtcccct gcgttcccca ctgtggccta ccgtgggt tttgcattgt gtttctagca    2220
ccgaggatct gagaacaagc ggagggccgg gccctgggac ccctgctcca gcccgaatga   2280
cggcatctgt ttgccatgta cctggatgcg acgggcccct ggggacaggc ccttgcccca   2340
tccatccgct tgaggcatgg caccgccctg catccctaat accaaatctg actccaaaat   2400
tgtggggtgt gacatacaag tgactgaaca cttcctgggg agctacaggg gcacttaacc   2460
caccacagca cagcctcatc aaaatgcagc tggcaacttc tccccaggt gccttccccc    2520 tgctgccggc ctttgctcct tcacttccaa catctctcaa aataaaaatc cctcttcccg   2580
ctctgagcga ttcagctctg cccgcagctt gtacatgtct ctcccctggc aaaacaagag   2640
ctgggtagtt tagccaaacg gcaccccctc gagttcactg cagacccttc gttcaccgtg   2700
tcacacatag aggggttctg agtaagaaca aaacgttctg ctgctcaagc cagtctggca   2760
agcactcagc ccagcctcga ggtccttctg gggagagtgt aagtggacag agtcctggtc   2820 aggggcagg agtgtcccaa gggctggccc acctgctgtc tgtctgctcc tcctagccct    2880
tggtcagatg gcagccagag tccctcagga cctgcagcct cgccccggca gaagtctttt   2940
gtccaggagg caaaaagcca gagattctgc aacacgaatt cgaagcaaac aaacacaaca   3000
caacagaatt cctggaaaga agacgactgc taagacacgg cagggggggcc tggagggagc   3060 ctccgactct gagctgctcc gggatctgcc gcgttctcct ctgcacattg ctgtttctgc   3120
ccctgatgct ggagctcaag gagactcctt cctctttctc agcagagctg tagctgactg   3180
tggcattact acgcctcccc acacgcccag acccctcact ccaaaatcct actggctgta   3240
```

```
gcagagaata cctttgaacc aagattctgt tttaatcatc atttacattg ttttcttcca    3300 aaggcccct cgtatacct ccctaaccca caaacctgtt aacattgtct taaggtgaaa      3360
tggctggaaa atcagtattt aactaataaa tttatctgta ttcctcttaa aaaaaaaaa     3419

<210> SEQ ID NO 5
<211> LENGTH: 23
<212> TYPE: DNA
<213> ORGANISM: Artificial Sequence
<220> FEATURE:
<223> OTHER INFORMATION: Forward primer for amplifying Gata4 gene

<400> SEQUENCE: 5
agcagctccg tgtcccagac gtt                                              23

<210> SEQ ID NO 6
<211> LENGTH: 26
<212> TYPE: DNA
<213> ORGANISM: Artificial Sequence
<220> FEATURE:
<223> OTHER INFORMATION: Reverse primer for amplifying Gata4 gene

<400> SEQUENCE: 6
ccaactcaca ggagagatgc agtgtg                                           26

<210> SEQ ID NO 7
<211> LENGTH: 1195
<212> TYPE: DNA
<213> ORGANISM: Homo sapiens

<400> SEQUENCE: 7
ctccatcctc tgcctcaccc agtccccgct gagactgagc agacgcctcc aggatctgtc     60
ggcagctgct gttctgaggg agagcagaga ccatgtctga catagaagag gtggtggaag    120
agtacgagga ggaggagcag gaagaagcag ctgttgaaga gaggaggac tggagagagg    180 acgaagacga gcaggaggag gcagcggaag gatgctgaa agcagaggct gagaccgagg    240
agaccagggc agaagaagat gaagaagaag aggaagcaaa ggaggctgaa gatggcccaa    300
tggaggagtc caaaccaaag cccaggtcgt tcatgcccaa cttggtgcct cccaagatcc    360
ccgatggaga gagagtggac tttgatgaca tccaccggaa gcgcatggag aaggacctga    420
atgagttgca ggcgctgatc gaggctcact ttgagaacag gaagaaagag gaggaggagc    480
tcgtttctct caaagacagg atcgagagac gtcgggcaga gcgggccgag cagcagcgca    540
tccggaatga gcgggagaag gagcggcaga accgcctggc tgaagagagg gctcgacgag    600
aggaggagga gaacaggagg aaggctgagg atgaggcccg gaagaagaag gctttgtcca    660
acatgatgca ttttgggggt tacatccaga gacagagcg gaaaagtggg aagaggcaga    720
ctgagcggga aaagaagaag aagattctgg ctgagaggag gaaggtgctg gccattgacc    780
acctgaatga agatcagctg agggagaagg ccaaggagct gtggcagagc atctataact    840
tggaggcaga gaagttcgac ctgcaggaga agttcaagca gcagaaatat gagatcaatg    900
ttctccgaaa caggatcaac gataaccaga agtctccaa gaccgcgggg aaggctaaag    960
tcaccgggcg ctggaaatag agcctggcct ccttcaccaa agatctgctc ctcgctcgca   1020
cctgcctccg gcctgcactc ccccagttcc cgggccctcc tgggcacccc aggcagctcc   1080
tgtttggaaa tggggagctg gcctaggtgg gagccaccac tcctgcctgc ccccacaccc   1140
actccacacc agtaataaaa agccaccaca cactgactgg caaaaaaaaa aaaaa        1195
```

```
<210> SEQ ID NO 8
<211> LENGTH: 20
<212> TYPE: DNA
<213> ORGANISM: Artificial Sequence
<220> FEATURE:
<223> OTHER INFORMATION: Forward primer for amplifying troponin T

<400> SEQUENCE: 8
ctcaaagaca ggatcgagag                                                   20

<210> SEQ ID NO 9
<211> LENGTH: 20
<212> TYPE: DNA
<213> ORGANISM: Artificial Sequence
<220> FEATURE:
<223> OTHER INFORMATION: Reverse primer for amplifying troponin T

<400> SEQUENCE: 9
gatcttcatt caggtggtca                                                   20

<210> SEQ ID NO 10
<211> LENGTH: 858
<212> TYPE: DNA
<213> ORGANISM: Homo sapiens

<400> SEQUENCE: 10
gagacaggga cagacgtagg ccaagagagg ggaaccagag aggaaccaga ggggagagac       60
agagcagcaa gcagtggatt gctccttgac gacgccagca tgagctcctt ctccaccacc     120
accgtgagct tcctcctttt actggcattc cagctcctag gtcagaccag agctaatccc     180
atgtacaatg ccgtgtccaa cgcagacctg atggatttca gaatttgct ggaccatttg      240 gaagaaaaga tgcctttaga agatgaggtc gtgcccccac aagtgctcag tgagccgaat     300
gaagaagcgg gggctgctct cagccccctc cctgaggtgc ctccctggac cggggaagtc     360
agcccagccc agagagatgg aggtgccctc gggcggggcc cctgggactc ctctgatcga     420
tctgccctcc taaaaagcaa gctgagggcg ctgctcactg cccctcggag cctgcggaga     480
tccagctgct tcgggggcag gatggacagg attggagccc agagcggact gggctgtaac     540
agcttccggt actgaagata acagccaggg aggacaagca gggctgggcc tagggacaga     600
ctgcaagagg ctcctgtccc ctggggtctc tgctgcattt tgtgtcatct gttgccatgg     660
agttgtgatc atcccatcta agctgcagct tcctgtcaac acttctcaca tcttatgcta     720
actgtagata aagtggtttg atggtgactt cctcgcctct cccacccat gcattaaatt      780 ttaaggtaga acctcacctg ttactgaaag tggtttgaaa gtgaataaac ttcagcacca     840
tggacagaag acaaaaaa                                                   858

<210> SEQ ID NO 11
<211> LENGTH: 20
<212> TYPE: DNA
<213> ORGANISM: Artificial Sequence
<220> FEATURE:
<223> OTHER INFORMATION: Forward primer for amplifying ANP

<400> SEQUENCE: 11
tccagctcct aggtcagacc                                                   20

<210> SEQ ID NO 12
<211> LENGTH: 20
<212> TYPE: DNA
<213> ORGANISM: Artificial Sequence
<220> FEATURE:
```

<223> OTHER INFORMATION: Reverse primer for amplifying ANP

<400> SEQUENCE: 12
tctgggctcc aatcctgtcc                                                                 20

<210> SEQ ID NO 13
<211> LENGTH: 1823
<212> TYPE: DNA
<213> ORGANISM: Homo sapiens

<400> SEQUENCE: 13
gagaagctag gggtgaggaa gccctggggc gctgccgccg cttttccttaa ccacaaatca         60
ggccggacag gagagggagg ggtgggggac agtgggtggg cattcagact gccagcactt        120
tgctatctac agccggggct cccgagcggc agaaagttcc ggccactctc tgccgcttgg        180
gttgggcgaa gccaggaccg tgccgcgcca ccgccaggat atggagctac tgtcgccacc        240
gctccgcgac gtagacctga cggccccga cggctctctc tgctcctttg ccacaacgga         300
cgacttctat gacgacccgt gtttcgactc cccggacctg cgcttcttcg aagacctgga        360
cccgcgcctg atgcacgtgg gcgcgctcct gaaacccgaa gagcactcgc acttccccgc        420
ggcggtgcac ccgccccgg gcgcacgtga ggacgagcat gtgcgcgcgc ccagcgggca        480
ccaccaggcg ggccgctgcc tactgtgggc ctgcaaggcg tgcaagcgca agaccaccaa        540
cgccgaccgc cgcaaggccg ccaccatgcg cgagcggcgc cgcctgagca agtaaatga        600
ggcctttgag acactcaagc gctgcacgtc gagcaatcca aaccagcggt tgcccaaggt        660
ggagatcctg cgcaacgcca tccgctatat cgagggcctg caggctctgc tgcgcgacca        720
ggacgccgcg ccccctggcg ccgcagccgc cttctatgcg ccgggcccgc tgccccggg        780
ccgcggcggc gagcactaca gcggcgactc cgacgcgtcc agcccgcgct ccaactgctc        840
cgacggcatg atggactaca gcggccccc gagcggcgcc cggcggcgga actgctacga        900
aggcgcctac tacaacgagg cgcccagcga acccaggccc gggaagagtg cggcggtgtc        960
gagcctagac tgcctgtcca gcatcgtgga gcgcatctcc accgagagcc ctgcggcgcc       1020
cgccctcctg ctggcggacg tgccttctga gtcgcctccg cgcaggcaag aggctgccgc       1080
ccccagcgag ggagagagca gcggcgaccc cacccagtca ccggacgccg ccccgcagtg       1140
ccctgcgggt gcgaaccca acccgatata ccaggtgctc tgaggggatg gtggccgccc       1200
acccgcccga gggatggtgc ccctagggtc cctcgcgccc aaaagattga acttaaatgc       1260
ccccctccca acagcgcttt aaaagcgacc tctcttgagg taggagaggc gggagaactg       1320
aagtttccgc cccgccca cagggcaagg acacagcgcg gttttttcca cgcagcaccc        1380
ttctcggaga cccattgcga tggccgctcc gtgttcctcg gtgggccaga gctgaacctt       1440
gaggggctag gttcagcttt ctcgcgccct cccccatggg ggtgagaccc tcgcagacct       1500
aagccctgcc ccgggatgca ccggttattt gggggggcgt gagacccagt gcactccggt       1560
cccaaatgta gcaggtgtaa ccgtaaccca ccccaaccc gtttcccggt tcaggaccac        1620
tttttgtaat acttttgtaa tctattcctg taaataagag ttgctttgcc agagcaggag       1680
cccctggggc tgtatttatc tctgaggcat ggtgtgtggt gctacaggga atttgtacgt       1740
ttataccgca ggcgggcgag ccgcgggcgc tcgctcaggt gatcaaaata aaggcgctaa       1800
tttataaaaa aaaaaaaaaa aaa                                              1823

<210> SEQ ID NO 14
<211> LENGTH: 22

```
<212> TYPE: DNA
<213> ORGANISM: Artificial Sequence
<220> FEATURE:
<223> OTHER INFORMATION: Forward primer for amplifying MyoD

<400> SEQUENCE: 14
gagcaatcca aaccagcggt tg                                              22

<210> SEQ ID NO 15
<211> LENGTH: 21
<212> TYPE: DNA
<213> ORGANISM: Artificial Sequence
<220> FEATURE:
<223> OTHER INFORMATION: Reverse primer for amplifying MyoD

<400> SEQUENCE: 15
tagtaggcgc cttcgtagca g                                               21

<210> SEQ ID NO 16
<211> LENGTH: 2084
<212> TYPE: DNA
<213> ORGANISM: Homo sapiens

<400> SEQUENCE: 16
gaccaagtga agctacaact tgcgacata  aattttgggg tctcgaacca tgtcgctgac       60
caacacaaag acggggtttt cggtcaagga catcttagac ctgccggaca ccaacgatga      120
ggagggctct gtggccgaag gtccggagga agagaacgag ggcccgagc cagccaagag       180 ggccgggccg ctggggcagg gcgccctgga cgcggtgcag agcctgcccc tgaagaaccc      240
cttctacgac agcagcgaca acccgtacac gcgctggctg gccagcaccg agggccttca      300
gtactccctg cacggtctgg ctgccggggc gccccctcag gactcaagct ccaagtcccc      360
ggagccctcg gccgacgagt caccggacaa tgacaaggag accccgggcg gcgggggga      420 cgccggcaag aagcgaaagc ggcgagtgct tttctccaag gcgcagacct acgagctgga      480
gcggcgcttt cggcagcagc ggtacctgtc ggcgcccgag cgcgaacacc tggccagcct      540
catccgcctc acgcccacgc aggtcaagat ctggttccag aaccaccgct acaagatgaa      600
gcgcgcccgg gccgagaaag ggcctggatc acagttcctc aagctttggg atacaaacga      660
atcacctggg atttggataa aatgcagatt cgtgttcagc agccctggca ttctgcattt      720
ctcatgagct ccagggagac gctggtgctg ctggggcagg accacacttt gggtggcaag      780
ggcttggcag gcaattccag gtgtcaccct agagatggcc tgctattgca ctgtcagtag      840
gtagctgcca cagtgacggc cgctccagat caaggggagg acctttgaa agggtccttt      900 gaatcatttg ggaaataaat caagccatat gagtaaaaag taatcaaaaa atatgttgaa      960
tattggaacc agaggaaatc ttagcatcat tttgtaatga ctccctccac gaattttcca     1020
gataaggaaa ctgacaaagc caggtggcct gtggctgagg agcgagacgg tcagcgaggt     1080
ctccctgctg cactctcgtg cacttccaca gtgaaaccct gctgagagac acaggaaatg     1140
ttgaacatag tgtcttttaaa attaagacta tgactgccct aaacatttac aaagcacaaa     1200
ccatgagaaa aaagcctgta ccagaaatca gaagatggcc tttgtccatg tgcaaccttg     1260
gacaagttaa ttacttatcg ctgctctctg agcccgtttc cccactggtt accgaaaaaa     1320
tagaaaagga tatgcctgcc cttcctaatt cacagggcat cgcagggagg taggtagtta     1380
atatgctgaa ccacttcaaa acggtggagc tgaactcaca gcaggaaccc tgtcacacct     1440
ttccatgaca aggatatcag tggggtgagg gaggtgggga gaggcatgag gatgggagac     1500
```

-continued

| | | | | | |
|---|---|---|---|---|---|
| aaaggagtgg | ggtgggggc | gggggaagga | ggaagccaga | aggacaggcc | caggctaggc | 1560 |
| tctgaagtca | gcaggtgagc | gaggtagaga | actagcagca | ccactgtcca | tggatatttg | 1620 |
| cggtgatgga | aatgtactgt | atccatgttc | tccaatatgg | cagccactag | ccacatgtgg | 1680 |
| ctatcaagcg | ctagaaatgt | agctagtgtg | atcgaggaac | tgatctttaa | ttttctttta | 1740 |
| attgttatta | atttccattt | aaatagccac | atgtggccag | tggcttatgt | agcaaagatc | 1800 |
| tagatcattt | gtttgaagca | gtaaaaagag | aaatgtgaat | cccctcttct | tacctcctat | 1860 |
| aacatgctaa | ttaacatcac | tgcaattaac | caccattcac | agctcttcag | ctgctctgtg | 1920 |
| gaacctcagc | ccactctgaa | atgaacagcc | gcagtggcag | gggttacaga | atgggctggg | 1980 |
| agtggcaatg | tagatttatc | tcttcacaca | ctctatgccc | tctatcaaaa | atgcctcagg | 2040 |
| ctgtgtaaaa | ttccacaaat | aataaagaga | ttttaaaaat | gtga | | 2084 |

<210> SEQ ID NO 17
<211> LENGTH: 19
<212> TYPE: DNA
<213> ORGANISM: Artificial Sequence
<220> FEATURE:
<223> OTHER INFORMATION: Forward primer for amplifying Nkx2.2

<400> SEQUENCE: 17
gacataaatt ttgggtct                                                  19

<210> SEQ ID NO 18
<211> LENGTH: 19
<212> TYPE: DNA
<213> ORGANISM: Artificial Sequence
<220> FEATURE:
<223> OTHER INFORMATION: Reverse primer for amplifying Nkx2.2

<400> SEQUENCE: 18
ggttctggaa ccagatctt                                                 19

<210> SEQ ID NO 19
<211> LENGTH: 3002
<212> TYPE: DNA
<213> ORGANISM: Homo sapiens

<400> SEQUENCE: 19

| | | | | | |
|---|---|---|---|---|---|
| ggggaggagg | ggagaacggg | gagcgcacag | cctggacgcg | tgcgcaggcg | tcaggcgcat | 60 |
| agacctgcta | gccctcagc | tagcggcccc | gcccgcgctt | agcatcacta | actgggctat | 120 |
| ataacctgag | cgcccgcgcg | gccacgcacac | gaggaattcg | cccacgcagg | aggcgcggcg | 180 |
| tccggaggcc | ccagggttat | gagactatca | ctgctcagga | cctactaaca | acaaaggaaa | 240 |
| tcgaaacatg | accaaatcgt | acagcgagag | tgggctgatg | ggcgagcctc | agccccaagg | 300 |
| tcctccaagc | tggacagacg | agtgtctcag | ttctcaggac | gaggagcacg | aggcagacaa | 360 |
| gaaggaggac | gacctcgaag | ccatgaacgc | agaggaggac | tcactgagga | acggggagga | 420 |
| ggaggaggac | gaagatgagg | acctggaaga | ggaggaagaa | gaggaagagg | aggatgacga | 480 |
| tcaaaagccc | aagagacgcg | gccccaaaaa | gaagaagatg | actaaggctc | gcctggagcg | 540 |
| ttttaaattg | agacgcatga | aggctaacgc | ccggagcgg | aaccgcatgc | acggactgaa | 600 |
| cgcggcgcta | gacaacctgc | gcaaggtggt | gccttgctat | tctaagacgc | agaagctgtc | 660 |
| caaaatcgag | actctgcgct | tggccaagaa | ctacatctgg | gctctgtcgg | agatcctgcg | 720 |
| ctcaggcaaa | agcccagacc | tggtctcctt | cgttcagacg | ctttgcaagg | gcttatccca | 780 |
| acccaccacc | aacctggttg | cgggctgcct | gcaactcaat | cctcggactt | ttctgcctga | 840 |

```
gcagaaccag gacatgcccc cccacctgcc gacggccagc gcttccttcc ctgtacaccc      900
ctactcctac cagtcgcctg ggctgcccag tccgccttac ggtaccatgg acagctccca      960
tgtcttccac gttaagcctc cgccgcacgc ctacagcgca gcgctggagc ccttctttga     1020
aagccctctg actgattgca ccagcccttc ctttgatgga cccctcagcc cgccgctcag     1080
catcaatggc aacttctctt tcaaacacga accgtccgcc gagtttgaga aaaattatgc     1140
ctttaccatg cactatcctg cagcgacact ggcaggggcc caaagccacg gatcaatctt     1200
ctcaggcacc gctgcccctc gctgcgagat ccccatagac aatattatgt ccttcgatag     1260
ccattcacat catgagcgag tcatgagtgc ccagctcaat gccatatttc atgattagag     1320
gcacgccagt ttcaccattt ccgggaaacg aacccactgt gcttacagtg actgtcgtgt     1380
ttacaaaagg cagccctttg ggtactactg ctgcaaagtg caaatactcc aagcttcaag     1440
tgatatatgt atttattgtc attactgcct ttggaagaaa caggggatca agttcctgt      1500 tcacccttatg tattattttc tatagctctt ctatttaaaa aataaaaaaa tacagtaaag     1560
tttaaaaaat acaccacgaa tttggtgtgg ctgtattcag atcgtattaa ttatctgatc     1620
gggataacaa aatcacaagc aataattagg atctatgcaa tttttaaact agtaatgggc     1680
caattaaaat atatataaat atatatttt caaccagcat tttactactt gttacctttc      1740
ccatgctgaa ttattttgtt gtgattttgt acagaatttt taatgactttt ttataatgtg     1800 gatttcctat tttaaaacca tgcagcttca tcaatttttta tacatatcag aaaagtagaa     1860
ttatatctaa tttatacaaa ataatttaac taatttaaac cagcagaaaa gtgcttagaa     1920
agttattgtg ttgccttagc acttctttcc tctccaattg taaaaaaaaa aaaaaaaaa      1980 aaaaaaaaa aaaattgca caatttgagc aattcatttc actttaaagt ctttccgtct      2040
ccctaaaata aaaaccagaa tcataatttt caagagaaga aaaattaag agatacattc      2100 cctatcaaaa catatcaatt caacacatta cttgcacaag cttgtatata catattataa     2160
ataaatgcca acatacccctt cttttaaatca aaagctgctt gactatcaca tacaatttgc    2220
actgttactt tttagtcttt tactccttttg cattccatga ttttacagag aatctgaagc    2280
tattgatgtt tccagaaaat ataaatgcat gatttttatac atagtcacaa aaatggtggt    2340
ttgtcatata ttcatgtaat aaatctgagc ctaaatctaa tcaggttgtt aatgttggga     2400
tttatatcta tagtagtcaa ttagtacagt agcttaaata aattcaaacc atttaattca     2460
taattagaac aatagctatt gcatgtaaaa tgcagtccag aataagtgct gtttgagatg     2520
tgatgctggt accactggaa tcgatctgta ctgtaatttt gtttgtaatc ctgtatatta     2580
tggtgtaatg cacaatttag aaaacattca tccagttgca ataaaatagt attgaaagtg     2640
agagcaattg ttgcatttct tcttaaaggg attctgtttt tattttttggg gaaagtagtt     2700 gcttttttgc tgagttaaaa aatactaaac actatatgta gaataaaaga aaagaaaaaa     2760
gtttaccttg gcatatgctc ttgtctgttt atccttgcaca gggagtcacc agttctatgt     2820
agataatgaa aagacctaac tgatatttca ttatttggaa tatgggactg gacggcagta     2880
caaacagtgt gttttttttct ttgttttaag tggcttagcc tttaggtttt ttatttccat     2940
ttttaaaaat gattgttaca tgttttcttc tatttctttt tttaaaaggt ggattttaat     3000
aa                                                                     3002
```

<210> SEQ ID NO 20
<211> LENGTH: 20
<212> TYPE: DNA

```
<213> ORGANISM: Artificial Sequence
<220> FEATURE:
<223> OTHER INFORMATION: Forward primer for amplifying NeuroD1

<400> SEQUENCE: 20
gcacaatttg agcaattcat                                              20

<210> SEQ ID NO 21
<211> LENGTH: 21
<212> TYPE: DNA
<213> ORGANISM: Artificial Sequence
<220> FEATURE:
<223> OTHER INFORMATION: Reverse primer for amplifying NeuroD1

<400> SEQUENCE: 21
caagcttgtg caagtaatgt g                                            21

<210> SEQ ID NO 22
<211> LENGTH: 2729
<212> TYPE: DNA
<213> ORGANISM: Homo sapiens

<400> SEQUENCE: 22
gaaggaagag gaagaggagg agagggaggc cagagccaga acagcccggc agcccgagct    60
tcggggagga acggcctgag ccccgagcaa gttgcctcgg gagccctaat cctctcccgc   120
tggctcgccg agcggtcagt ggcgctcagc ggcggcgagg ctgaaatatg ataatcagaa   180
cagctgcgcc gcgcgccctg cagccaatgg gcgcggcgct cgcctgacgt ccccgcgcgc   240
tgcgtcagac caatggcgat ggagctgagt tggagcagag aagtttgagt aagagataag   300
gaagagaggt gcccgagccg cgccgagtct gccgccgccg cagcgcctcc gctccgccaa   360
ctccgccggc ttaaattgga ctcctagatc cgcgagggcg cggcgcagcc gagcagcggc   420
tctttcagca ttggcaaccc caggggccaa tatttcccac ttagccacag ctccagcatc   480
ctctctgtgg gctgttcacc aactgtacaa ccaccatttc actgtggaca ttactccctc   540
ttacagatat gggagacatg ggagatccac caaaaaaaaa acgtctgatt tccctatgtg   600
ttggttgcgg caatcagatt cacgatcagt atattctgag ggtttctccg gatttggaat   660
ggcatgcggc atgtttgaaa tgtgcggagt gtaatcagta tttggacgag agctgtacat   720
gctttgttag gatgggaaaa acctactgta aaagagatta tatcaggttg tacgggatca   780
aatgcgccaa gtgcagcatc ggcttcagca agaacgactt cgtgatgcgt gcccgctcca   840
aggtgtatca catcgagtgt ttccgctgtg tggcctgcag ccgccagctc atccctgggg   900
acgaatttgc gcttcgggag acggtctctc tctgccgagc agaccacgat gtggtggaga   960
gggccagtct aggcgctggc gacccgctca gtcccctgca tccagcgcgg ccactgcaaa  1020
tggcagcgga gcccatctcc gccaggcagc cagccctgcg gccccacgtc cacaagcagc  1080
cggagaagac cacccgcgtg cggactgtgc tgaacgagaa gcagctgcac accttgcgga  1140
cctgctacgc cgcaaacccg cggccagatg cgctcatgaa ggagcaactg gtagagatga  1200
cggggctcag tccccgtgtg atccgggtct ggtttcaaaa caagcggtgc aaggacaaga  1260
agcgaagcat catgatgaag caactccagc agcagcagcc aatgacaaaa ctaatatcc   1320 agggatgac aggaactccc atggtggctg ccagtccaga gagacacgac ggtggcttac  1380
aggctaaccc agtggaagta caaagttacc agccaccttg gaaagtactg agcgacttcg  1440
ccttgcagag tgacatagat cagcctgctt ttcagcaact ggtcaatttt tcagaaggag  1500
gaccgggctc taattccact ggcagtgaag tagcatcaat gtcctctcaa cttccagata  1560
```

```
cacctaacag catggtagcc agtcctattg aggcatgagg aacattcatt ctgtatttt      1620 tttccctgtt ggagaaagtg ggaaattata atgtcgaact ctgaaacaaa agtatttaac     1680
gacccagtca atgaaaactg aatcaagaaa tgaatgctcc atgaaatgca cgaagtctgt     1740
tttaatgaca aggtgatatg gtagcaacac tgtgaagaca atcatgggat tttactagaa     1800
ttaaacaaca aacaaaacgc aaaacccagt atatgctatt caatgatctt agaagtactg     1860
aaaaaaaaag acgttttaa aacgtagagg atttatattc aaggatctca agaaagcat      1920 tttcatttca ctgcacatct agagaaaaac aaaaatagaa aattttctag tccatcctaa     1980
tctgaatggt gctgtttcta tattggtcat tgccttgcca acaggagct ccagcaaaag      2040 cgcaggaaga gagactggcc tccttggctg aaagagtcct ttcaggaagg tggagctgca     2100
ttggtttgat atgtttaaag ttgactttaa caaggggtta attgaaatcc tgggtctctt     2160
ggcctgtcct gtagctggtt tattttttac tttgcccct cccacttt ttttgagatcc       2220 atcctttatc aagaagtctg aagcgactat aaaggtttt gaattcagat ttaaaaacca     2280
acttataaag cattgcaaca aggttacctc tattttgcca caagcgtctc gggattgtgt     2340
ttgacttgtg tctgtccaag aacttttccc ccaaagatgt gtatagttat tggttaaaat    2400
gactgttttc tctctctatg gaataaaaa ggaaaaaaaa aaaggaaact tttttgttt      2460 gctcttgcat tgcaaaaatt ataaagtaat ttattattta ttgtcggaag acttgccact    2520
tttcatgtca tttgacattt tttgtttgct gaagtgaaaa aaaagataa aggttgtacg     2580 gtggtctttg aattatatgt ctaattctat gtgttttgtc ttttttctaa atattatgtg     2640
aaatcaaagc gccatatgta gaattatatc ttcaggacta tttcactaat aaacatttgg    2700
catagataaa taaataaaaa aaaaaaaaa                                      2729

<210> SEQ ID NO 23
<211> LENGTH: 18
<212> TYPE: DNA
<213> ORGANISM: Artificial Sequence
<220> FEATURE:
<223> OTHER INFORMATION: Forward primer for amplifying Islet1

<400> SEQUENCE: 23
ggctgttcac caactgta                                                    18

<210> SEQ ID NO 24
<211> LENGTH: 20
<212> TYPE: DNA
<213> ORGANISM: Artificial Sequence
<220> FEATURE:
<223> OTHER INFORMATION: Reverse primer for amplifying Islet1

<400> SEQUENCE: 24
actcgatgtg atacaccttg                                                  20

<210> SEQ ID NO 25
<211> LENGTH: 2057
<212> TYPE: DNA
<213> ORGANISM: Homo sapiens

<400> SEQUENCE: 25
atattgtgct tccaccactg ccaataacaa ataactagc aaccatgaag tgggtggaat       60 caatttttt aatttcccta ctaaatttta ctgaatccag aacactgcat agaaatgaat       120
atggaatagc ttccatattg gattcttacc aatgtactgc agagataagt ttagctgacc      180
```

```
tggctaccat attttttgcc cagtttgttc aagaagccac ttacaaggaa gtaagcaaaa      240
tggtgaaaga tgcattgact gcaattgaga acccactgg agatgaacag tcttcagggt       300
gtttagaaaa ccagctacct gcctttctgg aagaactttg ccatgagaaa gaaattttgg     360
agaagtacgg acattcagac tgctgcagcc aaagtgaaga gggaagacat aactgttttc    420
ttgcacacaa aaagcccact ccagcatcga tcccactttt ccaagttcca gaacctgtca     480
caagctgtga agcatatgaa gaagacaggg agacattcat gaacaaattc atttatgaga   540
tagcaagaag gcatcccttc ctgtatgcac ctacaattct tctttgggct gctcgctatg     600
acaaaataat tccatcttgc tgcaaagctg aaaatgcagt gaatgcttc caaacaaagg     660 cagcaacagt tacaaaagaa ttaagagaaa gcagcttgtt aaatcaacat gcatgtgcag   720
taatgaaaaa ttttgggacc cgaactttcc aagccataac tgttactaaa ctgagtcaga    780
agtttaccaa agttaatttt actgaaatcc agaaactagt cctggatgtg gcccatgtac    840
atgagcactg ttgcagagga gatgtgctgg attgtctgca ggatggggaa aaaatcatgt   900
cctacatatg ttctcaacaa gacactctgt caaacaaaat aacagaatgc tgcaaactga    960
ccacgctgga acgtggtcaa tgtataattc atgcagaaaa tgatgaaaaa cctgaaggtc   1020
tatctccaaa tctaaacagg ttttttaggag atagagattt taaccaatt tcttcagggg   1080 aaaaaaatat cttcttggca agttttgttc atgaatattc aagaagacat cctcagcttg    1140
ctgtctcagt aattctaaga gttgctaaag gataccagga gttattggag aagtgttttcc   1200 agactgaaaa ccctcttgaa tgccaagata aggagaaga agaattacag aaatacatcc     1260
aggagagcca agcattggca aagcgaagct gcggcctctt ccagaaacta ggagaatatt  1320
acttacaaaa tgcgtttctc gttgcttaca aaagaaagc cccccagctg acctcgtcgg    1380
agctgatggc catcaccaga aaaatggcag ccacagcagc cacttgttgc caactcagtg   1440
aggacaaact attggcctgt ggcgagggag cggctgacat tattatcgga cacttatgta   1500
tcagacatga aatgactcca gtaaaccctg gtgttggcca gtgctgcact tcttcatatg   1560
ccaacaggag gccatgcttc agcagcttgg tggtggatga acatatgtc cctcctgcat     1620 tctctgatga caagttcatt ttccataagg atctgtgcca agctcagggt gtagcgctgc   1680
aaacgatgaa gcaagagttt ctcattaacc ttgtgaagca aagccacaa ataacagagg    1740 aacaacttga ggctgtcatt gcagatttct caggcctgtt ggagaaatgc tgccaaggcc   1800
aggaacagga agtctgcttt gctgaagagg acaaaaact gatttcaaaa actcgtgctg     1860
ctttgggagt ttaaattact tcaggggaag agaagacaaa acgagtcttt cattcggtgt    1920
gaacttttct ctttaatttt aactgattta acactttttg tgaattaatg aaatgataaa    1980
gacttttatg tgagatttcc ttatcacaga aataaaatat ctccaaatgt ttccttttca    2040
aaaaaaaaaa aaaaaaa                                                    2057
```

<210> SEQ ID NO 26
<211> LENGTH: 23
<212> TYPE: DNA
<213> ORGANISM: Artificial Sequence
<220> FEATURE:
<223> OTHER INFORMATION: Forward primer for amplifying AFP

<400> SEQUENCE: 26
ccgaactttc aagccataa ctg                                              23

<210> SEQ ID NO 27
<211> LENGTH: 25

```
<212> TYPE: DNA
<213> ORGANISM: Artificial Sequence
<220> FEATURE:
<223> OTHER INFORMATION: Reverse primer for amplifying AFP

<400> SEQUENCE: 27
cacttctcca ataactcctg gtatc                                              25
```

METHOD FOR INDUCING DIFFERENTIATION OF PLURIPOTENT STEM CELLS IN VITRO

FIELD

The present invention relates to a method for inducing differentiation of pluripotent stem cells in vitro. More specifically, the present invention relates to a method for inducing differentiation of pluripotent stem cells into cells with the same phenotype and function as those of the Information Presenting Cells for Differentiation (IPCD) in vitro, the method comprising co-culturing pluripotent stem cells or cell population with high content of the pluripotent stem cells with damaged and/or dead cells as IPCD (including fragments of the damaged and/or dead cells).

BACKGROUND

In recent years, studies for inducing differentiation from pluripotent stem cells are under progress, and various kinds of cells which have been induced to differentiate are expected to be applied for various uses including regenerative medicine, study relating to development of a new pharmaceutical agent, and safety test for pharmaceuticals.

Regenerative medicine has tried to overcome diseases either by using autologous- or homogenenous-pluripotent stem cells, pluripotent stem cells stored in a bank, or transplantation of cells differentiated from those pluripotent stem cells. Furthermore, in studies relating to development of new medicines, it is expected to develop drugs for treating diseases by using purposive cells differentiated from pluripotent stem cells derived from healthy donor or disease-specific pluripotent stem cells obtained from a patient. Furthermore, for a safety test for pharmaceuticals, it is expected to use the differentiation-induced cells by toxicity screening of pharmaceuticals that are under development or have been already developed.

Because the cells intended to be employed for above uses can be used in the actual medical field or used industrially, it is necessary to stably obtain differentiation-induced cells from pluripotent stem cells with large scale. An attempt for differentiation of various kinds of cells from pluripotent stem cells has been reported, and a method that induces gene introduction into pluripotent stem cells during the process of induction (Patent Literature 1 or the like), and a method that includes administration of a set of cytokines to pluripotent stem cells (Patent Literature 2) are known. However, those methods are in most cases comprised of complicated multiple steps and a long term period is generally required to induce pluripotent stem cells into purposive cells (e.g., for several weeks). Furthermore, these methods are costly in most of cases.

On the other hand, a method for differentiating cardiac muscle cells without cytokine induction is also proposed (Non Patent Literature 1). According to the proposal, the method is based on subjecting cells to feeder-less culture, isolating the cells as single cells, and thereafter, plating the cells at high density, and then conducting adhesion culture. However, there is a problem that in a case where it is not possible to habituate the cells to feeder-less culture, it is difficult to differentiate the cell.

Furthermore, as one of the pluripotent stem cells which are the pre-condition for inducing differentiation, Multilineage-differentiating Stress Enduring cells (Muse) expressing Stage-Specific Embryonic Antigen-3 (SSEA-3) as a surface antigen, which have been found by Mr. Dezawa as one of the inventors of the present invention and are present in mesenchymal cellular fraction, can be exemplified as a typical example (Patent Literature 3; Non Patent Literature 2). Unlike induced pluripotent stem cells (iPS cells), embryonic stem cells (ES cells) that are known as other pluripotent stem cells, as well as neural stem/progenitor cells (NSPC), and umbilical cord blood stem cells (UCBC), Muse cells are easily obtainable. Further, unlike iPS cells, they do not have a tumor genicity nor do they require exogenous gene introduction for acquiring pluripotency.

Contribution made by Muse cells in the field of regenerative medicine has been widely known until now, and it can be found in the treatment of myocardial infarction, brain tumor, cerebral infarction, kidney disease, or the like (Patent Literature 4 or the like). For the treatment of myocardial infarction, for example, it is known that, when Muse cells are injected from vein and home to the infarct site, they differentiate into cardiac muscle cells to repair the infarcted cardiac tissue. Meanwhile, a mechanism in which Muse cells migrate to damaged site after administration is also gradually known. For example, it has been suggested that the migration factor like sphingosine-1-phospate (SIP) (damage signal), which is released from damaged tissue, is related thereto (Patent Literature 5). However, detailed mechanism of the differentiation of Muse cells into tissue-compatible cells in the damaged tissue is not yet clarified.

The treatment of diseases using Muse cells can be referred to as a strategy by which the treatment is enabled by a series of administration, migration, and differentiation of Muse cells at a state where "principle of the site" remains effective, specifically, in a state where damaged cells or their fragments still remain in situ such as in the site where inflammatory reaction associated with the damage occurs, for example, in the case of acute disease including myocardial infarction producing damage signal from the damaged site. However, in the case of a chronic disease in which the "principle of the site" has been already lost and the low amount of damaged signal, in the case of diseases where vascular flow is interrupted, or in the case of diseases which requires rare cell replacement, intravascular administration of Muse cells as described above may not be sufficient enough to repair tissues. As such, if it is possible to obtain in vitro, both stably and easily at low cost, a large amount of the desired cells from pluripotent stem cells like Muse cells by inducing differentiation, further application to various uses such as regenerative medicine, development of a new pharmaceutical agent, or safety test for pharmaceuticals can be achieved.

CITATION LIST

Patent Literature

[PTL 1] JP 2013-252081 A
[PTL 2] JP 2004-298087 A
[PTL 3] WO 2011/007900 A
[PTL 4] WO 2014/027684 A
[PTL 5] WO 2014/133170 A

Non Patent Literature

[NPL 1] Yang L, et al., Nature, Vol. 453, p. 524-528 (2008)
[NPL 2] Wakao, S, et al., Proc. Natl. Acad. Sci. USA, Vol. 108, p. 9875-9880 (2011)

SUMMARY

Technical Problem

A conventionally known method for differentiating pluripotent stem cells to various kinds of cells requires multi-step treatments so that it is difficult to prepare a great amount of homogeneous desired cells with a short period of time. Furthermore, it is difficult to exclude the possibility of generating tumorigenicity in cells differentiated from iPS cells which have been established by exogenous gene introduction. As such, an object of the present invention is to provide a method for producing, easily and with high efficiency, various differentiated cells that are homogeneous and highly functional.

Solution to Problem

The present inventors have found that, in vitro, Muse cells have a phagocytic property, and, according to phagocytosis of damaged and/or dead cells (including fragments of damaged and/or dead cells), Muse cells differentiate into those cells, and thus completed the present invention accordingly.

Specifically, the present invention provides as follows.

[1] A method for inducing differentiation of pluripotent stem cells in vitro into cells having the same phenotype and function as Information Presenting Cells for Differentiation (IPCD), the method comprising co-culturing pluripotent stem cells or cell population with high content of the pluripotent stem cells either with damaged and/or dead cells as IPCD, and/or fragments of said damaged and/or dead cells.

[2] The method according to [1] above, wherein the pluripotent stem cells phagocytize damaged and/dead cells as IPCD, and/or fragments of said damaged and/or dead cells.

[3] The method according to [1] or [2] above, wherein the pluripotent stem cells are SSEA-3-positive cells isolated from mesenchymal tissues of a body or cultured mesenchymal cells.

[4] The method according to any one of [1] to [3] above, wherein the pluripotent stem cells are CD105-positive.

[5] The method according to any one of [1] to [4] above, wherein the pluripotent stem cells are CD117-negative and CD146-negative. [6] The method according to any one of [1] to [5] above, wherein the pluripotent stem cells are CD117-negative, CD146-negative, NG2-negative, CD34-negative, vWF-negative, and CD271-negative.

[7] The method according to any one of [1] to [6] above, wherein the pluripotent stem cells are CD34-negative, CD117-negative, CD146-negative, CD271-negative, NG2-negative, vWF-negative, Sox10-negative, Snail-negative, Slug-negative, Tyrp1-negative, and Dct-negative.

[8] The method according to any one of [1] to [7] above, wherein the pluripotent stem cells have all of the following properties:
 (i) telomerase activity at low or under detection level;
 (ii) having the ability to differentiate into any of three germ layers;
 (iii) exhibiting no tumorigenic proliferation; and
 (iv) having self-renewal ability.

[9] The method according to any one of [1] to [8] above, wherein the ratio between the number of the pluripotent stem cells and the number of the damaged and/or dead cells as IPCD is 1:10,000 to 10,000:1. [10] The method according to any one of [1] to [9] above, wherein the damaged and/or dead cells as IPCD, and/or fragments of said damaged and/or dead cells are obtained by adding a pharmaceutical agent selected from the group consisting of apoptosis inducing agent, metabolic antagonist, alkylating agent, anthracycline, antibiotics, antimitotic agent, topoisomerase inhibitor, proteasome inhibitor, anti-cancer agent, heat, low temperature, acid, alkali, ultrasonic wave, and physical disruption by vortex or the like.

[11] The method according to any one of [1] to [10] above, wherein the IPCD are cells derived from ectoderm.

[12] The method according to [11] above, wherein the cells derived from ectoderm are selected from the group consisting of neural cells, glial cells, pigment cells, skin cells, inner ear cells, retinal cells, corneal cells, and hair follicle cells.

[13] The method according to any one of [1] to [10] above, wherein the IPCD are cells derived from mesoderm.

[14] The method according to [13] above, wherein the cells derived from mesoderm are selected from the group consisting of cardiac muscle cells, skeletal muscle cells, smooth muscle cells, osteocytes, chondrocytes, germ line cells, and hematopoietic cells.

[15] The method according to any one of [1] to [10] above, wherein the IPCD are cells derived from endoderm.

[16] The method according to [15] above, wherein the cells derived from endoderm are selected from the group consisting of pancreatic β cells, liver cells, bile duct cells, respiratory epithelial cells, esophageal epithelial cell, vascular endothelial cells, kidney-constituting cells, bladder epithelial cells, and pancreatic exocrine cells.

[17] The method according to any one of [1] to [10] above, wherein the IPCD are rare cells.

[18] The method according to [17] above, wherein the rare cells are selected from the group consisting of motor neuron, dopamine neuron, intermediate neuron, glutamine-activated neuron, pituitary gland cells, thyroid gland cells, adrenal cortex, adrenal medulla, pressure-sensor cells of carotid artery, heart conduction system, choroid plexus epithelial cells, pancreatic-alpha cells, pancreatic-delta cells, and lung Clara cells.

[19] A method for confirming in vitro that cells contained in a cell preparation are live pluripotent stem cells, including:
 (a) co-culturing cells in the cell preparation with damaged and/or dead cells, and/or fragments of said damaged and/or dead cells; and
 (b) if the cells in the cell preparation are differentiated into cells having the same phenotype and function as exodermal-lineage cells, mesodermal-lineage cells, and/or endodermal-lineage cells derived from the damaged and/dead cells, and/or fragments of said damaged and/or dead cells, determining that the pluripotent stem cells are alive in the cell preparation.

[20] A method for in vitro production of cells having the same phenotype and function as IPCD from pluripotent stem cells, the method comprising co-culturing pluripotent stem cells or cell population with high content of the pluripotent stem cells either together with damaged and/or dead cells as IPCE, and/or fragments of the damaged and/or dead cells.

Advantageous Effects of Invention

According to the present invention, by co-culturing pluripotent stem cells together with damaged and/or dead cells as IPCD, and/or together with fragments of the damaged and/or dead cells, the IPCD cell type is obtained from pluripotent stem cells. The differentiated cells that are obtained accordingly can be applied to various uses includ-

BRIEF DESCRIPTION OF DRAWINGS

FIGS. 1A and 1B illustrate the result of detecting mRNA expression of various markers when Muse cells are added for a case in which either culture supernatant or exosome obtained from intact mouse cardiac muscle cells is added to a culture system. FIG. 1C illustrates the result of determining the mRNA expression when Muse cells are directly contacted with intact mouse cardiac muscle cells. FIG. 1D illustrates, 3 days and 7 days after the culture based on direct contact, presence or absence of the expression of GATA-4 as determined by immunostaining and observed under a fluorescence microscope.

FIG. 7A is an image obtained by fluorescence microscopy, showing that Muse cells (green) express myogenin (red) as a marker for skeletal muscle cells. FIG. 7B shows differentiation of Muse cells into skeletal muscle cells, in which MyoD is used as an indicator.

DESCRIPTION OF EMBODIMENTS

Figure 1:
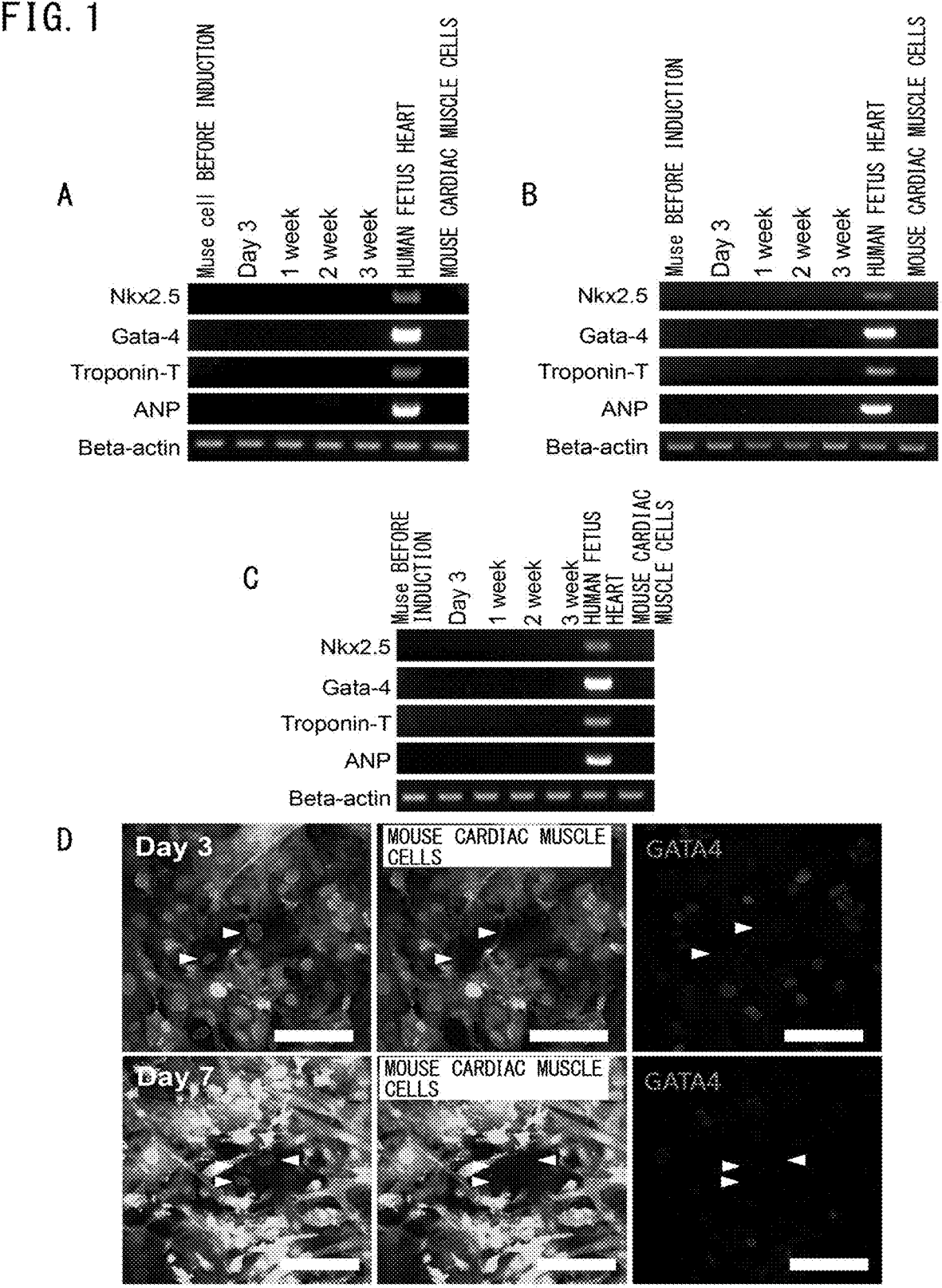
FIG. 1 is a view illustrating the result of determining the induction of differentiation using intact mouse cardiac muscle cells.

The present invention relates to, as a method for inducing differentiation of pluripotent stem cells in vitro, a method of obtaining cells having a same phenotype and function as cells which are an origin of damaged and/or dead cells by co-culturing pluripotent stem cells with damaged and/or dead cells. The present invention is described hereinbelow.

The present invention relates to a method for inducing differentiation of pluripotent stem cells in vitro into IPCD cell type, the method comprising co-culturing pluripotent stem cells or cell population with high content of pluripotent stem cells with damaged and/or dead cells as IPCD, and/or together with fragments of the damaged and/or dead cells as IPCD. According to the present invention, as damaged and/or dead cells, and/or fragments of the damaged and/or dead cells are phagocytized by the pluripotent stem cells during co-culturing, the pluripotent stem cells can be differentiated into cells having the same phenotype and function as the original IPCD from which the damaged cells or the like are derived. With regard to the phagocytic property of pluripotent stem cells, in particular, Muse cells, it is known until now that Muse cells phagocytize ferrite (magnetic material) (JP 2016-028614 A), but the mechanism of differentiation of Muse cells, as information-receiving cells, into the cell type of phagocytosed damaged cell or the like, which are IPCD, is not known. As described above, the present invention is based on finding for the first time that, as Muse cells phagocytize damaged cells or the like, they can differentiate into original IPCD phenotype which are the origin of the damaged cells or the like. Although in vitro induction of differentiation utilizing the phagocytic property of those pluripotent stem cells is achieved by simple co-culturing of the pluripotent stem cells with damaged cells or the like, the method for obtaining damaged cells or the like, and the method for co-culturing can be easily carried out based on a means that is commonly employed by a person who is skilled in the pertinent art, and thus not limited.

According to one embodiment, the present invention can be a method for in vitro induction of differentiation of pluripotent stem cells, including:
 (a) step of culturing IPCD;
 (b) step of damaging or destroying the IPCD in the above culture system; and
 (c) step of adding pluripotent stem cells to the culture system of the step (b) and carrying out culturing.
 Furthermore, according to another embodiment, the present invention can be in vitro induction of differentiation of pluripotent stem cells, including:
 (a') step of culturing pluripotent stem cells;
 (b') step of obtaining damaged and/or dead cells as IPCD, and/or fragments of said damaged and/or dead cells by damaging or destroying IPCD; and
 (c') step of adding the damaged and/or dead cells as IPCD, and/or fragments of the damaged and/or dead cells as IPCD that are obtained from the step (b) to the culture system of the step (a) and carrying out culturing.

(1) Pluripotent Stem Cells

The pluripotent stem cells to be used in the cell preparation and pharmaceutical composition of the present invention are typically cells that reside in the human body. The cells which are named "Muse (Multilineage-differentiating Stress Enduring) cells" were discovered by Prof. Dezawa, one of the present inventors. Muse cells can be obtained from bone marrow aspirates and adipose tissue (Ogura, F., et al., Stem Cells Dev., Nov. 20, 2013 (Epub) (published on Jan. 17, 2014)) or from skin tissue such as dermal connective tissue, and they are widely dispersed throughout the connective tissue of various organs. The cells have the properties of both pluripotent stem cells and mesenchymal stem cells, and are identified as cells double-positive for the cell surface markers "SSEA-3 (Stage-specific embryonic antigen-3)" and "CD105". Therefore, Muse cells or cell populations containing Muse cells, for example, can be isolated from body tissue using these antigen markers. Muse cells are also stress-tolerant, and can be concentrated from mesenchymal tissue or cultured mesenchymal cells by different types of stress treatments. A cell fraction in which Muse cells were enriched into high content by stress treatment may be used as the cell preparation of the present invention. The methods of separation and identification of Muse cells, and their features, are disclosed in detail in International Patent Publication No. WO2011/007900. Also, as reported by Wakao et al. (2011, ibid.), all of Muse cells isolated from the bone marrow- or skin-derived mesenchymal cells were both positive for SSEA-3 and CD105. According to the present invention, in cases where Muse cells are isolated from mesenchymal tissue of a body or cultured mesenchymal stem cells SSEA-3 can be simply used as the antigen marker for the purpose of isolating Muse cells. Throughout the present specification, pluripotent stem cells (Muse cells) or a cell population containing Muse cells, which were isolated from mesenchymal tissue of a body or cultured mesenchymal tissue by using SSEA-3 as the antigen marker, and which can be used in in the method for inducing differentiation according to the present invention, may be referred to simply as "SSEA-3 positive cells". Also throughout the present specification, "non-Muse cells" refers to cells that are present in mesenchymal tissue of a body or cultured mesenchymal tissue, and are the remainder of "SSEA-3 positive cells".

In brief, Muse cells or a cell population containing Muse cells can be isolated from body tissue (for example, mesenchymal tissue) using only antibody for the cell surface marker SSEA-3, or using antibodies for both SSEA-3 and CD105. The term "body" here means "mammalian body". According to the present invention, the "body" does not include a fertilized ovum or an embryo at a developmental stage before the blastocyst stage, but it does include an embryo at the developmental stage from the blastocyst stage onward, including the fetus or blastocyst. The mammal is not limited to a certain species and may be a primate such as human or monkey, a rodent such as a mouse, rat, rabbit or guinea pig, or a cat, dog, sheep, pig, cow, horse, donkey, goat or ferret. The Muse cells to be used in the cell preparation and pharmaceutical composition of the present invention are clearly distinguished from embryonic stem cells (ES cells) or iPS cells in terms of direct separation from body tissue by using a specified marker. The term "mesenchymal tissue" refers to tissue from the bone, synovial membrane, fat, blood, bone marrow, skeletal muscle, dermis, ligament, tendon, dental pulp, umbilical cord or umbilical cord blood, or tissues present in various organs. For example, the Muse cells may be obtained from the bone marrow or skin or adipose tissue. Preferably, mesenchymal tissue of a body is harvested and the Muse cells are isolated from the tissue and used. The separating means mentioned above may be used to separate Muse cells from cultured mesenchymal cells such as fibroblasts or bone marrow-derived MSCs. The Muse cells to be used for the cell preparation and pharmaceutical composition of the present invention may be either autologous or allogenic with respect to the recipient.

As mentioned above, Muse cells or a cell population containing Muse cells can be isolated from body tissue by using SSEA-3 positivity, or double positive for SSEA-3 and CD105, as indicators, but human adult skin is known to include various types of stem cells and progenitor cells. However, Muse cells are not identical to these cells. Such stem cells and progenitor cells include skin-derived precursors (SKP), neural crest stem cells (NCSC), melanoblasts (MB), perivascular cells (PC), endothelial precursor cells (EP) and adipose-derived stem cells (ADSC). Muse cells can be separated out as being "non-expressing" for the markers unique to these cells. More specifically, Muse cells can be separated by using non-expression for at least one, and for example, 2, 3, 4, 5, 6, 7, 8, 9, 10 or 11 among 11 markers selected from the group consisting of CD34 (EP and ADSC marker), CD117 (c-kit) (MB marker), CD146 (PC and ADSC marker), CD271 (NGFR) (NCSC marker), NG2 (PC marker), vWF factor (von Willebrand factor) (EP marker), Sox10 (NCSC marker), Snail (SKP marker), Slug (SKP marker), Tyrp1 (MB marker) and Dct (MB marker). As a non-limitative example, non-expression of CD117 and CD146 may be used as the indicator for separation, non-expression of CD117, CD146, NG2, CD34, vWF and CD271 may be used as the indicator, or non-expression of all of the aforementioned 11 markers may be used as the indicator for separation.

The Muse cells having the aforementioned features to be used for the cell preparation and pharmaceutical composition of the present invention may have at least one property selected from the group consisting of the following:

(i) telomerase activity at low or under detection level;
(ii) having the ability to differentiate into cells of the three germ layers;
(iii) exhibiting no tumorigenic proliferation; and
(iv) having self-renewal ability.

According to one aspect of the present invention, the Muse cells to be used for the cell preparation and pharmaceutical composition of the present invention have all of these properties. As regards (i), "telomerase activity at low or under detection level", this refers to low level or the level under detection limit telomerase activity when using a TRAPEZE XL telomerase detection kit (Millipore), for example. "Low" telomerase activity is, for example, either telomerase activity on the same level as somatic cells such as human fibroblasts, or telomerase activity of $\frac{1}{5}$ and preferably no greater than $\frac{1}{10}$ of that of Hela cells. In regard to (ii), the Muse cells have the ability to differentiate into the three germ layers (endoderm, mesoderm and ectoderm) in vitro and in vivo, and by induction culturing in vitro, for example, they can differentiate into hepatocytes, neurons, skeletal muscle cells, smooth muscle cells, osteocytes or adipocytes. They may also exhibit the ability to differentiate into the three germ layers in the case of transplanting in vivo into the testes. They also have the ability to migrate to and engraft onto damaged organs (heart, skin, spine, liver, muscle, etc.), by administration into the body via intravenous injection, and differentiate into specific cells of the corresponding tissue. In regard to (iii), the Muse cells have the property of proliferating at a rate of about every 1.3 days in suspension culture, and growing in suspension culture from a single cell to form an embryoid-like cell mass, slow down the growth at about 14 days; however, when the embryoid-like cell mass is transferred to adhesion culture, cell growth resumes and the proliferated cells spread out from the cell mass. They also have the property of not generating teratomas at least for 6 months after transplantation into the testes. In regard to (iv), Muse cells have self-renewal (auto-replicating) ability. The term "self-renewal" means that cells in the embryoid-like cell mass obtained by culturing a single Muse cell in suspension culture can be confirmed to differentiate into cells of all 3 germ layers, and also that when a single cell from the embryoid-like cell mass is again carried into a suspension culture, it forms a next generation embryoid-like cell mass, and reproduce differentiation into three germ layers as well as embryoid-like cell mass in the suspension culture can be confirmed. Self-renewal may be observed once or as several repeated cycles.

In addition, a cell fraction containing Muse cells to be used in the cell preparation of the present invention may be a cell fraction having the SSEA-3 positive and CD105-positive pluripotent stem cells concentrated, obtained by a method of applying external stress treatment to mesenchymal tissue of a body or cultured mesenchymal cells, causing the cells other than the external stress-resistant cells to die, and recovering the surviving cells, the cell fraction having at least one and preferably all of the following properties.
  (i) SSEA-3 positivity;
  (ii) CD105-positivity;
  (iii) telomerase activity at low or under detection level;
  (iv) having the ability to differentiate into cells of the three germ layers;
  (v) exhibiting no neoplastic proliferation activity; and
  (vi) having self-renewal ability.

The external stress may be any one or a combination of: protease treatment, culturing in a low oxygen concentration, culturing under low-phosphate conditions, culturing with low serum concentration, culturing under low nutritive conditions, culturing under exposure to heat shock, culturing at low temperature, freezing treatment, culturing in the presence of a hazardous substance, culturing in the presence of active oxygen, culturing under mechanical stimulation, culturing with agitating treatment, culturing with pressure treatment, or physical impact. For example, the treatment time with a protease is preferably a total of 0.5 to 36 hours to apply external stress to the cells. The protease concentration may be the concentration used when the cells adhering to a culture vessel are detached, when the cell mass is dispersed into individual cells, or when individual cells are recovered from tissue. The protease is preferably a serine protease, aspartic acid protease, cysteine protease, metalloprotease, glutamic acid protease or N-terminal threonine protease. The protease is also preferably trypsin, collagenase or dispase.

(2) Information-Presenting Cells (IPCD)

The "IPCD" that are used in the in vitro method for inducing differentiation of pluripotent stem cells means the cells that have the same phenotype and function as cells that are in a state where the cells are terminally differentiated from pluripotent stem cells; are not subjected to any differentiation induction; and become an origin of damaged cells or dead cells. The origin of IPCD used in the present invention is allowed to be any type of species and cell type as long as desired differentiated phenotype is induced from pluripotent stem cells. For example, origin of the cells can have, depending on the purpose, various kinds of mammals as an origin, and although not limited thereto, the cells are derived from human, chimpanzee, other primates, domesticated animals such as dog or cat, livestock such as cow, pig, horse, or goat, test animals such as rabbit, rat, mouse, or guinea pig, or the like.

(3) Damaged Cells and Dead Cells

According to the present invention, the damaged and/or dead cells that are used for differentiating pluripotent stem cells into purposive cells can have the aforementioned IPCD as an origin. When used in the present specification, the term "damaged cells" indicates cells that are damaged by artificial stress or environmental stress, for example, and thus it is difficult for the damaged cells to proliferate even at appropriate culture conditions. Further, their metabolic activity is lower than general living cells, but are still higher dead cells.

When used in the present specification, the term "dead cells" indicates cells which cannot proliferate anymore even when they are cultured at appropriate culture conditions, and do not exhibit any metabolic activity. The "dead cells" can be any of dead cells caused by necrosis or apoptosis. Furthermore, according to the present invention, the phagocytic activity of pluripotent stem cells can be exhibited not for entire the damaged and/or dead cells but also for cellular organisms of the damaged and/or dead cells (e.g., cytoplasm, cell membrane, nucleus, mitochondria, Golgi body, endoplasmic reticulum, cell skeleton included in cytoplasm, enzyme, protein, RNA, and DNA) or cell debris.

Method for obtaining damaged cells, dead cells, and/or fragments of the damaged and/or dead cells from IPCD can be carried out based on a commonly used method, although it is not limited thereto. In the case of producing damaged cells, a pharmaceutical for inhibiting cell proliferation as it is known in the corresponding technical field can be used, for example. As for the pharmaceutical, although not limited thereto, those capable of reducing in significant sense the cell percentage in S phase can be mentioned, and, typically, a pharmaceutical which blocks the progress of cell division cycle, for example, pharmaceuticals for causing G1 stoppage and M phase stoppage are included. Specific examples of a reagent that can be used for producing damaged cells include metabolic antagonist/anti-cancer agent (e.g., azathioprine, 6-mercaptopurine, 6-thioguanine, fludarabine, pentostatin, cladribine, 5-fluorouracil (5FU), floxuridine (FUDR), cytosine arabinoside (cytarabine), methotrexate, trimethoprim, pyrimethamine, pemetrexed, capecitabine, gemcitabine, cytarabine); alkylating agent (e.g., cyclophosphamide, mechlorethamine, uramustine, melphalan, chlorambucil, thiotepa/chlorambucil, ifosfamide, carmustine, lomustine, streptozocin, busulfan, dibromomannitol, cisplatin, carboplatin, nedaplatin, oxaliplatin, satraplatin, triplatin tetranitrate, procarbazine, altretamine, dacarbazine, mitozolomide, temozolomide); anthracycline (e.g., daunorubicin, doxorubicin, epirubicin, idarubicin, valrubicin); antibiotics (e.g., dactinomycin, bleomycin, mitramycin, anthramycin, streptozotocin, gramicidin D, mitomycins (e.g., mitomycin C), duocarmycins (e.g., CC-1065), calicheamicins); antimitotic agent (maytansinoids, auristatins, dolastatins, cryptophycins, vincaalkaloid (e.g., vincristine, vinblastine, vindesine, vinorelbine), taxanes (e.g., paclitaxel, docetaxel), and colchicines; topoisomerase inhibitor (e.g., irinotecan, topotecan, amsacrine, etoposide, teniposide, mitoxantrone); and proteasome inhibitor (e.g., peptidyl boronic acid). Furthermore, with regard to the use of those reagents, concentration or use method of the reagents, conditions for culturing, and the like are the same as those that are generally carried out, and they can be suitably set by a person who is skilled in the pertinent art. For example, when the aforementioned reagents are used, suitable concentration for obtaining damaged cells is preferably 1 to 100 μM, although it can be modified depending on the type of a reagent to be used.

According to another embodiment, a means for producing damaged cells can be, other than use of the reagents as described in the above, a method that is carried out by performing UV irradiation and/or X ray treatment for IPCD is possible. UV irradiation and X ray treatment can be performed by suitably selecting conditions that are known in the technical field. Furthermore, UV irradiation and X ray treatment can be also performed in conjunction with the use of the above reagents.

Reagents usable for production of the above damaged cells are included in reagents which can be used for producing dead cells, and the IPCD can be obtained by increasing the concentration or by prolonging the treatment time period of these reagents, for example. Furthermore, when UV irradiation or X ray treatment is selected for generating IPCD, it is also possible that the time for irradiation or the like is extended or the intensity of UV or X ray is increased, for example.

According to another embodiment, as a means for producing damaged and/or dead cells, methods like maintaining in a high temperature, maintaining a low temperature, treating with acid or alkali, treating by ultrasonication or vortex, performing freeze-thawing, treating with low oxygen, treating at low nutrition, treating with active oxygen, or the like can be mentioned, although it is not limited thereto. With regard to the use of the means, it can be used by a person who is skilled in the pertinent art after suitably selecting the conditions.

The method of the present invention may also include a means for judging the success or failure of the production of damaged and/or dead cells which were obtained by the above method. Included in a means for judgements are, although not limited thereto, observation under microscope, use of commercially available kit for measuring cell damage, and physiological or immunological measurement of materials secreted from cells, or the like. Among the dead cells, with regard to the dead cells in which cells are dead due to apoptosis, judgement can be made based on observation of unique morphological abnormality like cell surface curvature, condensation of nucleus chromatin, fragmentation of chromosome DNA or the like. Furthermore, for quantitative measurement of dead cells, a method of staining dead cells with trypan blue or colorimetric analysis using tetrazolium (MTT analysis) can be used.

(4) Conditions for Co-Culture

The present invention relates to a method for inducing differentiation of pluripotent stem cells in vitro by co-culturing pluripotent stem cells with damaged cells, dead cells, and/or together with fragments of the damaged and/or dead cells. As described in the present specification, the term "co-culture" means culturing two or more kinds of cells (or fragments thereof) under the same environment, and it indicates culturing the pluripotent stem cells and damaged cells or the like after adding them, each in predetermined number, to the same culture vessel or petri dish. Examples of an embodiment of the co-culture include (i) a system in which damaged cells or the like are added to pluripotent stem cells for co-culture, (ii) a system in which, after producing damaged cells or the like from IPCD, pluripotent stem cells are added thereto for co-culture, and (iii) a system in which co-culturing is performed in a culture vessel while pluripotent stem cells and damaged cells or the like are mixedly present in predetermined number.

Ratio between the number of the pluripotent stem cells and the number of the damaged and/or dead cells as IPCD is 1:10,000 to 10,000:1, and it is 1:10,000, 1:7,000, 1:5,000, 1:3,000, 1:2,000, 1:1,000, 1:700, 1:500, 1:300, 1:200, 1:100, 1:70, 1:50, 1:30, 1:20, 1:10, 1:7, 1:5, 1:3, 1:2, 1:1, 2:1, 3:1, 5:1, 7:1, 10:1, 20:1, 30:1, 50:1, 70:1, 100:1, 200:1, 300:1, 500:1, 700:1, 1,000:1, 2,000:1, 3,000:1, 5,000:1, 7,000:1, or 10,000:1, for example. It is sufficient that the culture solution for culturing cells is a medium in which cells for actual culture are cultured, and DMEM, RPMI-1640, Ham's F12, or the like can be used, in general. Furthermore, antibiotics, fetal bovine serum, antibiotics for selecting gene-incorporated cells, or the like that are commonly used can be added at a concentration of 0.1 to 10%.

Culture conditions like temperature for culture should follow common conditions for cell culture, and it is 36 to 38° C., and preferably 37° C., and also they can be under 4 to 6% $CO_2$, and preferably 5% $CO_2$ atmosphere, for example. Furthermore, time for the co-culturing is, although it depends on the type of cells which have been finally obtained after induction, roughly 2 to 10 days or so.

(5) Induction of Differentiation

As described in the present invention, the expression "induction of differentiation" means, by a certain means, leading pluripotent stem cells to differentiate into cell types which constitute specific organs, or tissues, or progenitor cells of these organs and tissues, but the expression also includes differentiation into cells that are belonging to a certain categorized such as endodermal-lineage cells, mesodermal-lineage cells, and exodermal-lineage cells. According to the present invention, inducing differentiation of pluripotent stem cells into specific cell type is achieved simply by co-culturing the pluripotent stem cells with damaged cells or the like, and it is characterized in that except for damaged cells and like, reagents or UV irradiation, or the like is not required. This differentiation induction is based on the phagocytic activity of pluripotent stem cells against damaged cells or the like, and it has been demonstrated that the differentiation induction is not caused by direct contact between pluripotent stem cells and IPCE, not by a certain humoral factor or exosome that are secreted from corresponding IPCD before damage or death, or IPCD after damage or death (see, Example 1).

Differentiation of pluripotent stem cells can be confirmed by a means which has been carried out in the corresponding technical field, and, typically, it can be carried out by examining the presence or absence of gene expression or protein expression of a predetermined differentiation marker in cells. Examples of a means include RT-PCR, Northern blot, flow cytometry, Western blot, and ELISA. For example, differentiation of pluripotent stem cells into cardiac muscle cells can be examined by mRNA level of gene expression of Nkx2.5 (NK-2 transcription factor related, locus 5), GATA-4, troponin-T, or ANP (atrial sodium diuretic peptide) as a differentiation marker for cardiac muscle cells being confirmed in differentiated pluripotent stem cells by using RT-PCR (Example 3, etc.).

(6) Use

By utilizing the property of pluripotent stem cells that they differentiate into cells derived from damaged cells, dead cells, or fragments of the damaged and/or dead cells according to phagocytosis of damaged cells, dead cells, or fragments of the damaged and/or dead cells, application can be made to quality management of a cell preparation containing pluripotent stem cells. According to the present invention, provided is a method for confirming in vitro that cells contained in a cell preparation are live pluripotent stem cells, the method including:

(a) co-culturing cells in a cell preparation with damaged cells, dead cells, and/or fragments of the damaged and/or dead cells; and (b) if the cells in a cell preparation are differentiated into cells having the same phenotype and function as exodermal-lineage cells, mesodermal-lineage cells, and/or endodermal-lineage cells to which the damaged cells, dead cells, and/or fragments of the damaged and/or dead cells belong, determining that the pluripotent stem cells are alive in the cell preparation.

Herein, the method for confirming whether or not the pluripotent cells (e.g., Muse cells) have differentiated into cell of three germ layer (exodermal-lineage cells, mesodermal-lineage cells, and endodermal-lineage cells) can be achieved by examining the presence or absence of expression of various cell markers as described in the above.

According to the present invention, it is possible to provide a method for in vitro production of cells having the same phenotype and function as those of IPCD from pluripotent stem cells, the method comprising co-culturing pluripotent stem cells or cell population with high content of pluripotent stem cells with damaged and/or dead cells as IPCD, and/or with fragments of the damaged and/or dead cells.

The present invention will now be explained in more specific detail through the following examples, with the understanding that the present invention is in no way limited by the examples.

EXAMPLES

Example 1: Analysis of Mechanism of Differentiation Induction in Muse Cells

According to a damage signal produced from damage site in a body (e.g., S1P), Muse cells migrate to and home into the damage site, and, after engraftment, differentiation of Muse cells are induced due to "principle of the site". However, the detailed mechanism for controlled differentiation of Muse cells is unknown. The example demonstrates in vitro analysis how differentiation induction is initiated in Muse cells. Elucidation of the mechanism how Muse cells receive the information of "principle of site", i.e., elucidation of factors that are relevant to differentiation induction, is a basis for application of Muse cells to chronic diseases in which the "principle of the site" has been lost, or regeneration of tissues or organs for which approach through blood vessels is difficult to make or regeneration of rare cells.

As for the style how Muse cells receive "principle of the site", there are possible mechanisms; humoral factor or exosome that are secreted from IPCD, or direct contact with IPCD without being mediated by those factors or the like, or phagocytosis of damaged IPCD by Muse cells, and the like. As such, by using intact mouse cardiac muscle cells and damaged mouse cardiac muscle cells, possibility of inducing differentiation of Muse cells by humoral factor, exosome, and direct contact among the above was determined.

(1) Induction of Differentiation by Using Intact Mouse Cardiac Muscle Cells

Intact mouse cardiac muscle cells, which have been established from the primary culture of neonatal heart 1 day after birth in C57BL/6-TG (CAG-EGFP) purchased from Japan SLC, Inc., were cultured for 10 days or so. After that, culture supernatant of the cells was collected and used as a material for determining the possibility of inducing differentiation caused by humoral factor. Next, culture supernatant of the above cardiac muscle cells, which have been cultured for 3 days in serum-free medium, was collected and the culture supernatant was admixed with ExoQuick Exosome Precipitation Solution (System Biosciences) followed by centrifuge to isolate exosomes secreted from cardiac muscle cells (see, Douglas, D., et al., Molecular Biology, 728 (4), 235 to 246 (2011)). The presence of exosomes was confirmed by Western blot in which HSP70 is used as a marker.

Next, human Muse cells were obtained according to the method described in WO 2011/007900 A. Muse cells were plated to culture dish (Nunc multidish 6 nunclon delta SI, Thermo, #140675) at the cell density $1\times10^4$ cells/well, and cultured for 24 hours. Subsequently, the culture supernatant derived from intact mouse cardiac muscle cells, which has been obtained from above, or exosomes were added thereto and the culture for 3 Days, 1 week, 2 weeks, and 3 weeks. Muse cells were collected at each time pint and an investigation was made to see whether or not the Muse cells differentiated into IPCD cell type, namely, cardiac muscle cells. Specifically, total RNA was collected from Muse cells, total RNA was extracted, and examined the expression of human specific-Nkx 2.5 (NK-2 transcription factor related, locus 5), GATA-4, troponin-T, and ANP (atrial sodium diuretic peptide) in RT-PCR. Nkx 2.5 and GATA-4 were selected as an initial differentiation marker which is expressed in cardiac muscle progenitor cells, ANP was selected as a premature cardiac muscle cell marker, and troponin-T was selected as a mature cardiac muscle marker. Human fetus heart was selected as positive control in RT-PCR and mouse cardiac muscle cells as negative control subject. As illustrated in FIG. 1, Muse cells did not express any of human cardiac muscle cell markers when intact mouse cardiac muscle cell-derived humoral factor (culture supernatant) (FIG. 1A) and exosome (FIG. 1B) were supplied.

Primers used for various markers as a detection subject in RT-PCR were designed and synthesized based on the nucleotide sequence of Nkx 2.5 (NM_004387; SEQ ID NO: 1), GATA-4 (NM_002052; SEQ ID NO: 4), troponin-T (NM_000364; SEQ ID NO: 7), and ANP (NM_006172; SEQ ID NO: 10). Specifically, they are described in the followings.

```
(1) Nkx 2.5
Forward primer:
                                        (SEQ ID NO: 2)
5'-CAGGACCAGACTCTGGAGCTG-3'
(corresponding to 821-841 nt of SEQ ID NO: 1)

Reverse primer:
                                        (SEQ ID NO: 3)
5'-CGCCGAAGTTCACGAAGTTGT-3'
(corresponding to 1118-1098 nt of SEQ ID NO: 1)

(2) GATA-4
Forward primer:
                                        (SEQ ID NO: 5)
5'-AGCAGCTCCGTGTCCCAGACGTT-3'
(corresponding to 1683-1705 nt of SEQ ID NO: 4)

Reverse primer:
                                        (SEQ ID NO: 6)
5'-CCAACTCACAGGAGAGATGCAGTGTG-3'
(corresponding to 2139-2114 nt of SEQ ID NO: 4)

(3) Troponin-T
Forward primer:
                                        (SEQ ID NO: 8)
5'-CTCAAAGACAGGATCGAGAG-3'
(corresponding to 489-508 nt of SEQ ID NO: 7)

Reverse primer:
                                        (SEQ ID NO: 9)
5'-GATCTTCATTCAGGTGGTCA-3'
(corresponding to 795-771 nt of SEQ ID NO: 7)

(4) ANP
Forward primer:
                                        (SEQ ID NO: 11)
5'-TCCAGCTCCTAGGTCAGACC-3'
(corresponding to 149-168 nt of SEQ ID NO: 10)

Reverse primer:
                                        (SEQ ID NO: 12)
5'-TCTGGGCTCCAATCCTGTCC-3'
(corresponding to 523-504 nt of SEQ ID NO: 10)
```

Subsequently, investigation was made to examine whether or not human Muse cells can be differentiated to cardiac muscle cell type under the direct contact with intact mouse cardiac muscle cells. First, green fluorescent protein (GFP) gene was introduced into intact mouse cardiac muscle cells. Next, GFP-labeled mouse cardiac muscle cells were plated to culture dish (Nunc multidish 6 nunclon delta SI, Thermo, #140675) at the cell density of $3 \times 10^4$ cells/well then human Muse cells of which nucleus have been labeled with DAPI in advance were added thereto at $1 \times 10^4$ cells/well, and co-cultured. At 3 Days, 1 week, 2 weeks, and 3 weeks after co-culture, cells were all collected and subjected to RT-PCR for validation of human specific-cardiac marker expression in human Muse cells (FIG. 1C) as described above. Like the result of the aforementioned supernatant and exosome administration, expression of markers for human cardiac muscle cells was not detected. Furthermore, 3 days and 7 days after the culture, presence or absence of GATA-4 expression was examined by immunostaining, and the results obtained by observation under a fluorescence microscope are shown in FIG. 1D. From Muse cells of which nucleus have been labeled with blue color, expression of GATA-4 was not recognized. From the above results, it was found that differentiation of Muse cells is not induced by cellular contact and/or interaction with intact mouse cardiac muscle cells.

(2) Induction of Differentiation by Using Damaged Mouse Cardiac Muscle Cells

Figure 2:
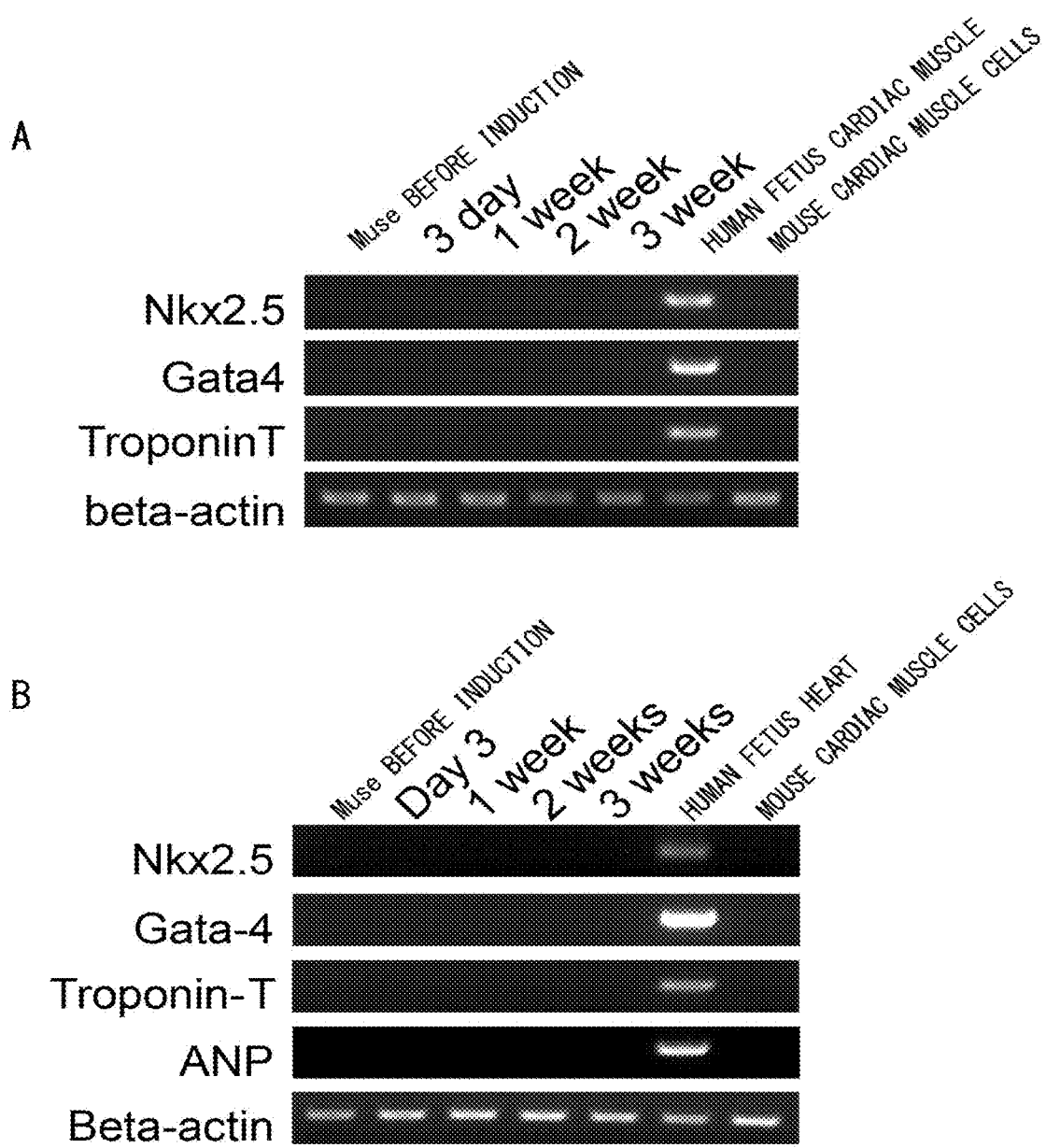
FIG. 2 illustrates the result of determining the induction of differentiation using damaged mouse cardiac muscle cells. It is the result of detecting mRNA expression of various markers when Muse cells are added for a case in which either culture supernatant or exosome obtained from damaged mouse cardiac muscle cells is added to a culture system (FIGS. 2A and 2B, respectively).

Investigation was performed to examine whether or not Muse cells can differentiate into cardiac muscle cell type when damaged mouse cardiac muscle cells are used. Production of damaged mouse cardiac muscle cells was carried out by using etoposide, which induces apoptosis. Simply, GFP-labeled mouse cardiac muscle cells were plated at $3 \times 10^4$ cells/well, and 2 days after the culture, 50 µM etoposide (SIGMA, #E1383) was added thereto. One day after the culture, the culture supernatant was collected from apoptotic mouse cardiac muscle cells, and were added to human Muse cells plated at $1 \times 10^4$ cells/well. At 3 Days, 1 week, 2 weeks, and 3 weeks after starting the culture, the expression of human specific for cardiac muscle cell markers were examined by RT-PCR (FIG. 2A) similar to intact mouse cardiac muscle cell expression. However, because none of the markers were detected, it was found that Muse cells differentiation into cardiac muscle cell type was not induced by culture supernatant of damaged cells.

Furthermore, investigation was also made by using exosomes secreted from the damaged mouse cardiac muscle cells. Human Muse cells were plated at the same cell density as described above, and then added exosomes. At 3 Days, 1 week, 2 weeks, and 3 weeks after the addition of exosomes, the expression of human specific mRNA was examined by RT-PCR (FIG. 2B) similar to the above. Differentiation of Muse cells into cardiac muscle cell type was not induced by the addition of an exosome like the result of using the culture supernatant.

Example 2: Determination of Phagocytic Property of Muse Cells

It has been reported that Muse cells can phagocytize ferrite. However, it was not determined whether or not Muse cells can also phagocytize damaged cells, dead cells, or fragments of the damaged and/or dead cells. As such, the phagocytic property of Muse cells was examined again by using PKH26PCL beads.

Figure 3:
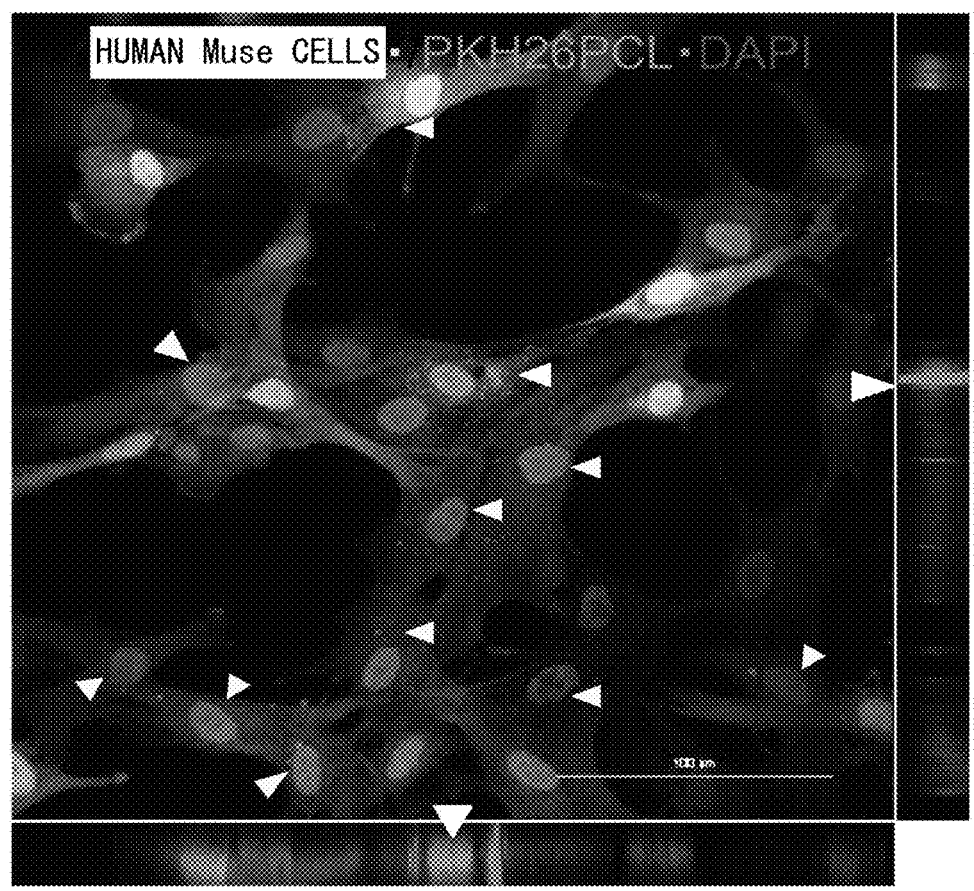
FIG. 3 illustrates the result of determining the phagocytic property of Muse cells. To determine the phagocytic capacity, PKH26PCL (red) was used.

PKH26PCL ($1 \times 10^{-3}$ M stock in ethanol; SIGMA, #PKH26PCL) is a pigment which can selectively label the cells having phagocytic capacity like macrophages, neutrophils, and microglial cells, and it is widely used in the pertinent art. First, GFP-Muse cells (green) counter stained by DAPI (blue) were cultured and then added with PKH26PCL (red). After that, the Muse cells were cultured for another 24 hours. As it is illustrated in FIG. 3, PKH126 was confirmed to be incorporated into the cytoplasm of Muse cells, and thus Muse cells were demonstrated to have phagocytic activity. About 74.1±4.6% of Muse cells were shown to phagocytose PKH26PCL.

Example 3: Induction of Differentiation by Co-Culturing Muse Cells and Damaged Cells The possibility that differentiation of Muse cells is induced by phagocytosis of damaged cells so as to directly receive the information of "principle of the site" was examined.

(1) Induction of Differentiation into Mesodermal Cells (Cardiac Muscle Cells)

Figure 4:
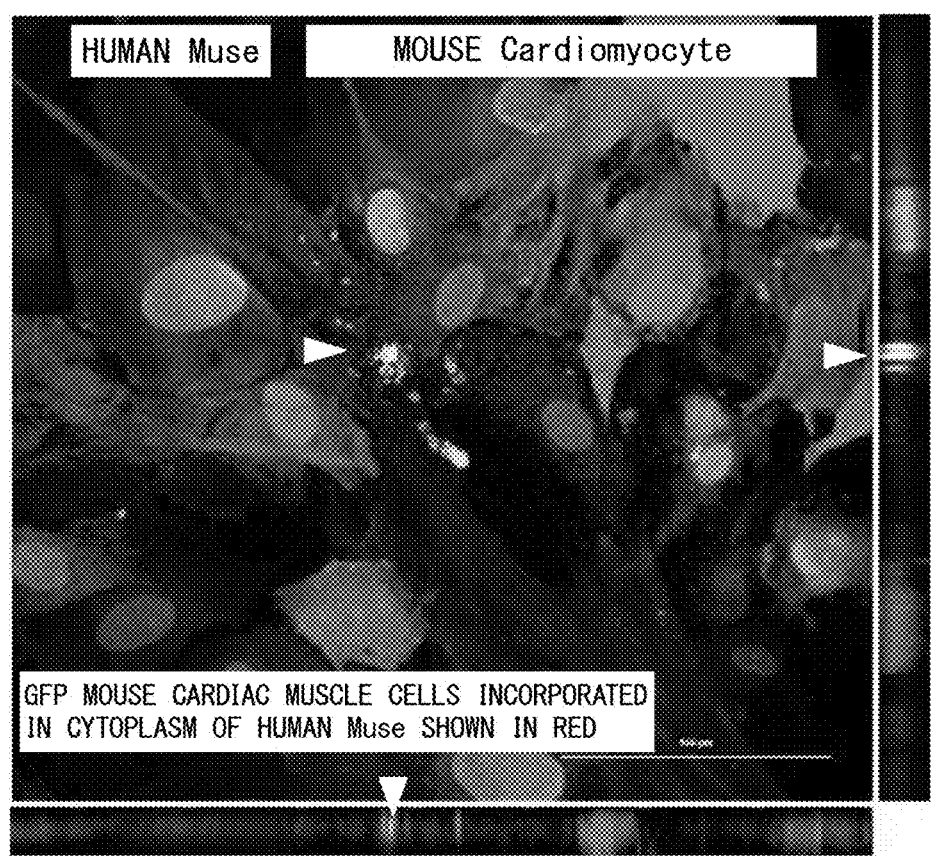
FIG. 4 illustrates the phagocytic property of Muse cells for damaged cardiac muscle cells. With regard to Muse cells co-cultured with GFP mouse cardiac muscle cells having induced apoptosis, fragments of the damaged cardiac muscle cells (green) is uptaken into the Muse cells (red).

Damaged cardiac muscle cells were prepared by using etoposide, which is a topoisomerase inhibitor. GFP-labeled mouse cardiac muscle cells prepared in Example 1 were used as IPCD. The GFP mouse cardiac muscle cells were plated at cell density $3 \times 10^4$ cells/well. One day after, 50 µM etoposide was added and then cultured for 1 day. Then, labeled human Muse cells were added at $1 \times 10^4$ cells/well followed by co-culturing. At 3 Days after co-culture, the phagocytosis of damaged cardiac muscle cells by Muse cells was examined under a fluorescence microscope. As it is illustrated in FIG. 4, GFP+fragments (green) of the damaged cardiac muscle cells is incorporated inside the Muse cells (red), and thus the phagocytic capacity of Muse cells was confirmed.

Figure 5:
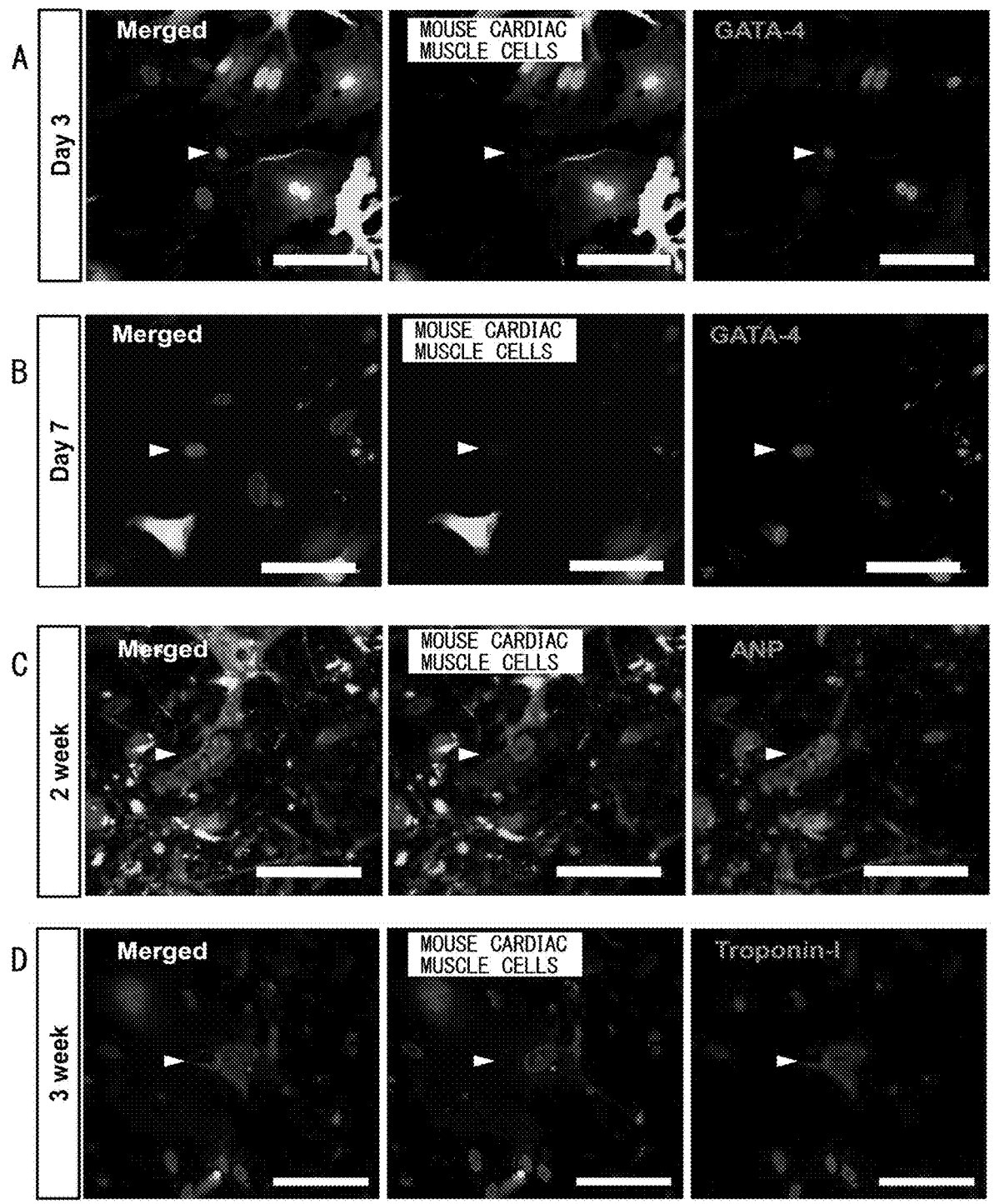
FIG. 5 illustrates induction of differentiation into cardiac muscle cells. Similar to FIG. 3, it illustrates the result of observing, under a fluorescence microscope, expression of various cardiac muscle markers with regard to the mode of induced differentiation of Muse cells, which have been co-cultured with GFP mouse cardiac muscle cells having induced apoptosis, into cardiac muscle cells.

Next, in the same co-culture system, 3 days, 1 week, 2 weeks, and 3 weeks after starting the co-culture, cells were fixed and it was examined whether or not the Muse cells were induced to differentiate into cardiac muscle cells. The differentiation induction in Muse cells was examined by carrying out immunostaining for GATA-4 (cardiac muscle progenitor cell marker), ANP (premature cardiac muscle cell marker), and troponin-I (mature marker for cardiac muscle cells) as a differentiation marker for cardiac muscle cells. The results are shown in FIG. 5. Muse cells which have been co-cultured with apoptotic cardiac muscle cells expressed GATA-4 on Day 3 and Day 7 (FIGS. 5A and 5B, respectively). Furthermore, Muse cells expressed ANP at 2 weeks and expressed troponin-1 at 3 weeks (FIGS. 5C and 5D, respectively). Since any kind of the differentiation markers has been expressed, it was confirmed that Muse cells have differentiated, by co-culturing with damaged cardiac muscle cells, into cardiac muscle cell types, which are mesodermal-lineage cells.

Figure 6:
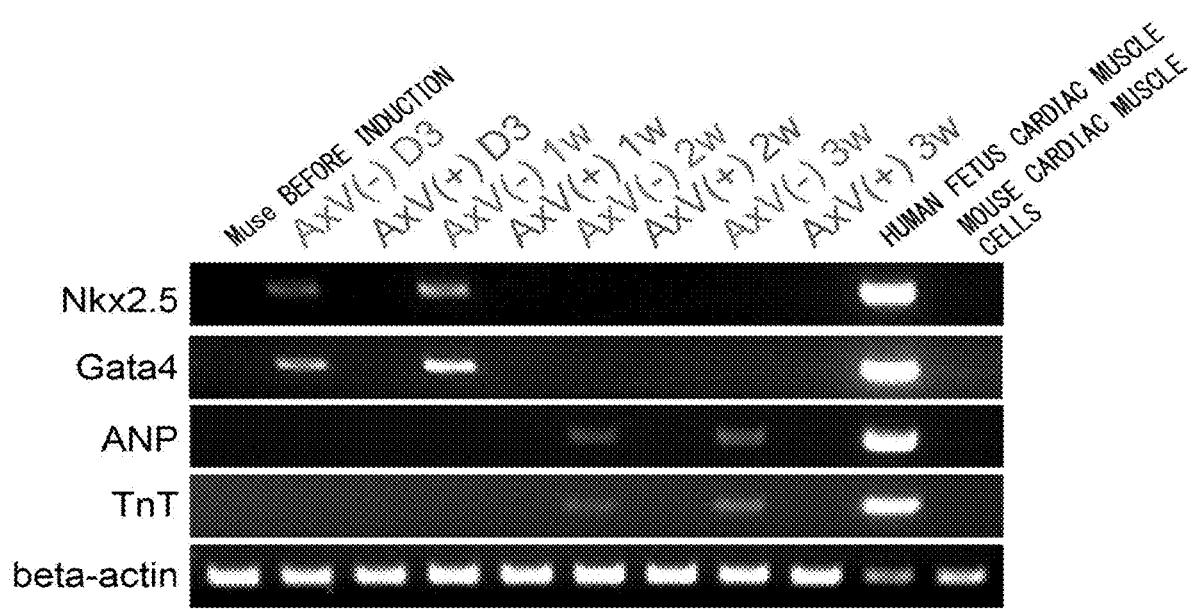
FIG. 6 illustrates the result of suppressing induction of differentiation by inhibiting the phagocytosis by Annexin V.

Furthermore, in order to validate that the induced differentiation of Muse cells into cardiac muscle cells described above is caused by the phagocytosis of damaged cardiac muscle cells, Annexin V was added to the culture system, and examined how suppression of phagocytosis affect on Muse cell differentiation. To the same culture system as the above co-culture, etoposide (50 µM) was added. After one day, 1 µg/mL Annexin V was added thereto followed by culture for 8 hours. After that, Muse cells ($1 \times 10^4$ cells/well) were added and the co-culture was continued. At 3 Days, 1 week, 2 weeks, and 3 weeks after adding Annexin V, total RNA was extracted from all the cells, and the presence or absence of the expression of each marker gene was examined by RT-PCR (FIG. 6).

Nkx 2.5 and GATA4 are differentiation markers expressed in cardiac muscle cells which are at early stage of differentiation and more juvenile. In samples without Annexin V (after 3 days and after 1 week), Muse cells have differentiated into cardiac muscle. However, in a sample with Annexin V, expression of cardiac differentiation markers was not observed. Also ANP and troponin T (TNT), markers for later than progenitor stage, were not observed in Muse cells with Annexin V. Accordingly, it was shown that, since the differentiation into cardiac muscle cells is inhibited by inhibition of phagocytotic activity in Muse cells, it is reasonable to consider that Muse cells obtain the information of "principle of site" for differentiation by phagocytizing dead cells or dying cells (damaged cells).

(2) Differentiation into Mesodermal Cells (Skeletal Muscle Cells)

Figure 7:
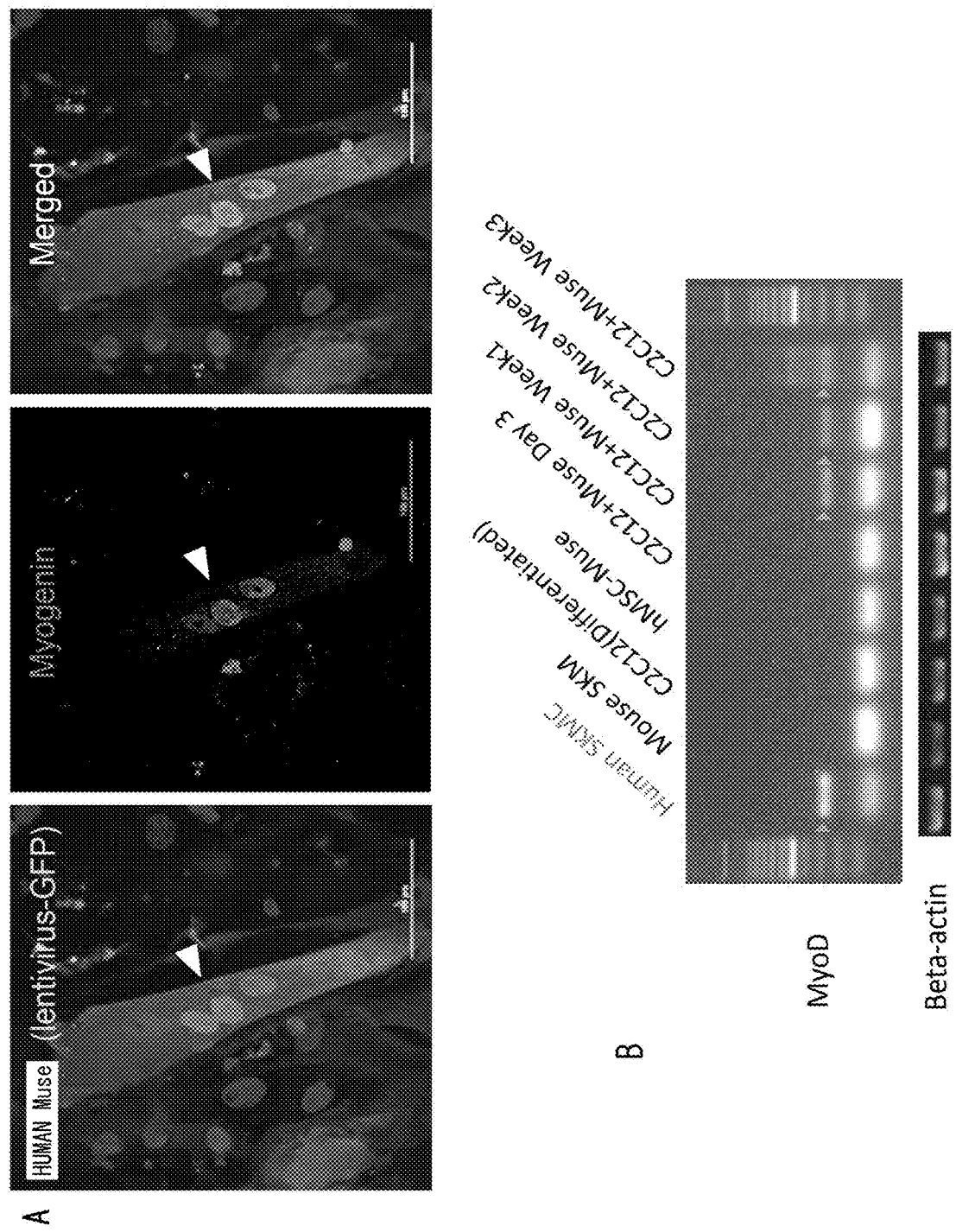
FIG. 7 illustrates the result of inducing differentiation into skeletal muscle cells.
Figure 8:
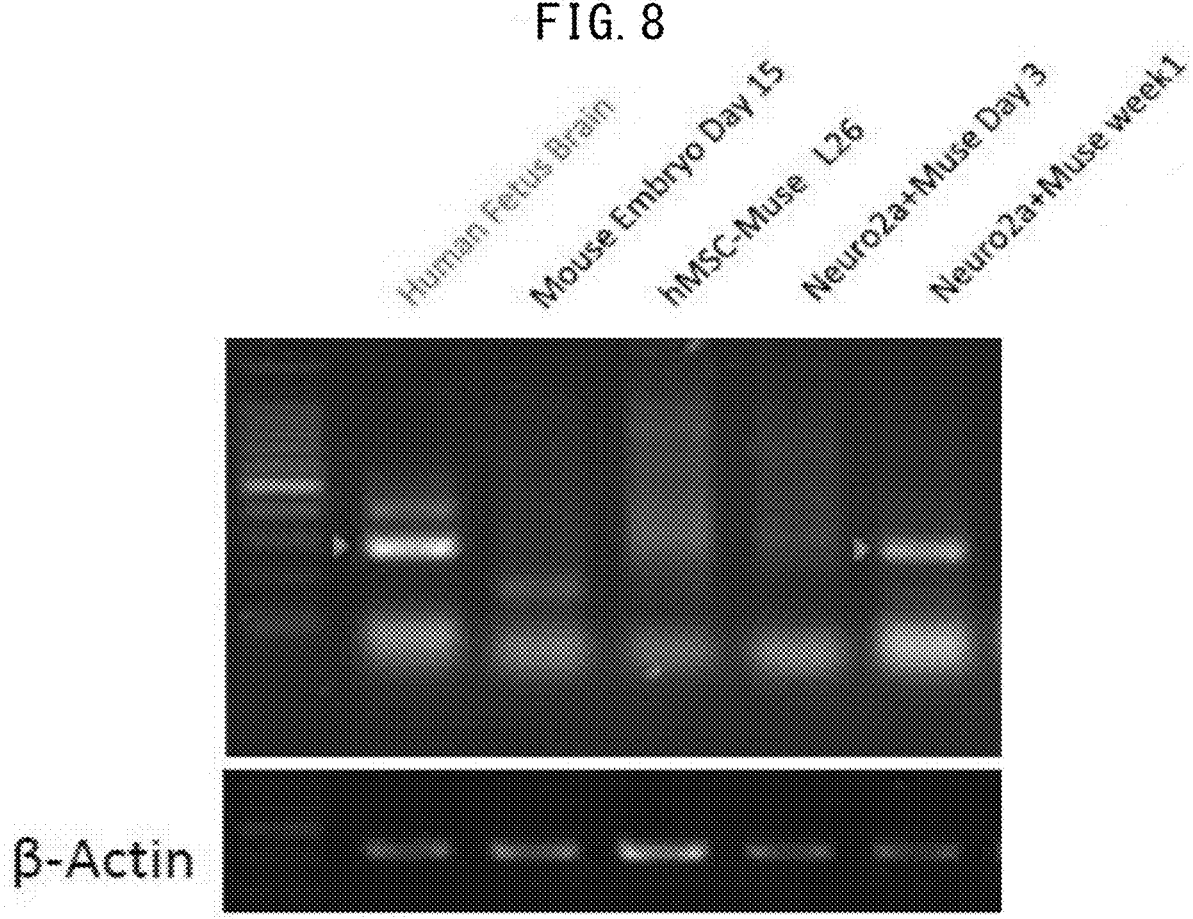
FIG. 8 illustrates the result of inducing differentiation into neural progenitor cells. It shows differentiation of Muse cells into neural cells, in which Neuro2A is used as an indicator.

By using mouse C2C12 (cell line derived from rhabdomyosarcoma) (ATCC, #CRL-1772), induced differentiation of Muse cells into mesodermal-lineage cell type was examined. C2C12 cells treated with etoposide were co-cultured with GFP-labeled Muse cells for induction of differentiation. Specifically, C2C12 cells were plated at cell density of $5 \times 10^4$ cells/well, treated with etoposide as described above, and then further plated Muse cells at the same cell density co-culturing. At 14 Days after starting the co-culture, the presence or absence of the expression of myogenin (differentiation marker for skeletal muscle cells) was examined by immunostaining. The result of observation under a fluorescence microscope and the result of RP-PCR for MyoD expression are shown in FIGS. 7A and 7B, respectively. Considering that Muse cells (green) with multi nuclei expressed myogenin (red), and also mRNA expression of MyoD was confirmed (1 week after starting the co-culture), it was shown that co-culture with damaged C2C12 induced differentiation into skeletal muscle cell type that belong to mesodermal-lineage cells.

Furthermore, primers used for various markers as a detection subject in RT-PCR were designed and synthesized based on the nucleotide sequence of MyoD (NM_002478; SEQ ID NO: 13). Specifically, they are described in the followings.

```
Forward primer:
                                          (SEQ ID NO: 14)
5'-GAGCAATCCAAACCAGCGGTTG-3'
(corresponding to 631-652 nt of SEQ ID NO: 13)

Reverse primer:
                                          (SEQ ID NO: 15)
5'-TAGTAGGCGCCTTCGTAGCAG-3'
(corresponding to 912-892 nt of SEQ ID NO: 13)
```

(3) Differentiation into Ectodermal-Lineage Cells (Neural Cells)

By using apoptotic neural cells (Neuro2A, ATCC, #CCL-131), differentiation of Muse cells into ectodermal cells was examined. Similar to the above, etoposide treated neural cells were prepared and then co-cultured with Muse cells. From the Muse cells, total RNA was extracted at 3 days and 1 week after starting the co-culture, and then evaluated. More specifically, mRNA expression of NeuN, which is known as a marker for neural cells, was examined by RT-PCR. Mouse embryo (cultured for 15 days) and human MSC-Muse cells (L26) did not express NeuN. On the other hand, after co-culture with apoptotic Neuro2A, expression of NeuN was confirmed in Muse cells, 1 week after starting the co-culture. Thus, it was shown that, according to co-culture with damaged neural cells, differentiation of Muse cells into neural cells, which belong to ectodermal-lineage cells, is yielded.

(4) Differentiation into Endodermal-Lineage Cells (β Cells)

Figure 9:
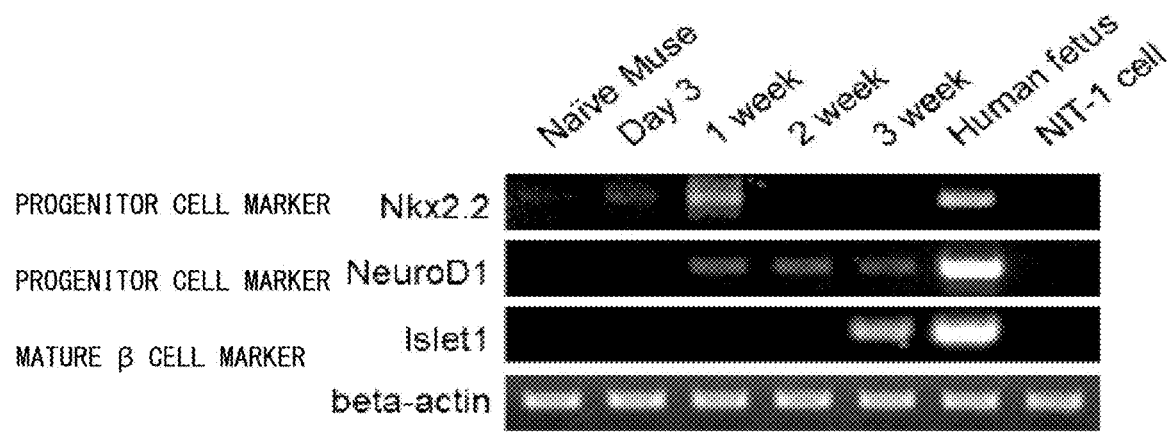
FIG. 9 illustrates the result of inducing differentiation into β cells. It shows differentiation of Muse cells into β cells, in which progenitor cell marker (Nkx2.2 and NeuroD1) and mature β cell marker (Islet1) are used as an indicator.

By using apoptotic mouse β cells (NIT-1) (ATCC, #CRL-2055), differentiation of Muse cells into endodermal-lineage cells was examined. Similar to the above experiment, etoposide treated apoptotic β cells were prepared and then co-cultured with Muse cells. From the Muse cells, total RNA was extracted at 3 days after and 1 to 3 weeks after starting the co-culture, and examined for Muse cell differentiation. More specifically, mRNA expression of Nkx 2.2 and NeuroD1, markers for β cell progenitor cells, and mRNA expression of Islet1, a mature β cell marker, were examined by RT-PCR. As it is illustrated in FIG. 9, from the change in expression of various markers over time, it was examined that Muse cells differentiated from progenitor cells to mature β cells according to the time course of co-culture. It was shown that, according to co-culture with damaged β cells, differentiation of Muse cells into β cells, which belong to endodermal-lineage cells, is yielded.

Furthermore, primers used for various markers as a detection subject in RT-PCR were designed and synthesized based on the nucleotide sequence of Nkx 2.2 (NM_002509; SEQ ID NO: 16), NeuroD1 (NM_002500; SEQ ID NO: 19), and Islet1 (NM_002202; SEQ ID NO: 22). Specifically, they are described in the followings.

```
1) Nkx 2.2
Forward primer:
                                          (SEQ ID NO: 17)
5'-GACATAAATTTTGGGGTCT-3'
(corresponding to 25-43 nt of SEQ ID NO: 16)

Reverse primer:
                                          (SEQ ID NO: 18)
5'-GGTTCTGGAACCAGATCTT-3'
(corresponding to 584-566 nt of SEQ ID NO: 16)

2) NeuroD1
Forward primer:
                                          (SEQ ID NO: 20)
5'-GCACAATTTGAGCAATTCAT-3'
(corresponding to 1998-2017 nt of SEQ ID NO: 19)

Reverse primer:
                                          (SEQ ID NO: 21)
5'-CAAGCTTGTGCAAGTAATGTG-3'
(corresponding to 2144-2124 nt of SEQ ID NO: 19)

3) Islet1
Forward primer:
                                          (SEQ ID NO: 23)
5'-GGCTGTTCACCAACTGTA-3'
(corresponding to 490-507 nt of SEQ ID NO: 22)

Reverse primer:
                                          (SEQ ID NO: 24)
5'-ACTCGATGTGATACACCTTG-3'
(corresponding to 858-839 nt of SEQ ID NO: 22)
```

Figure 10:
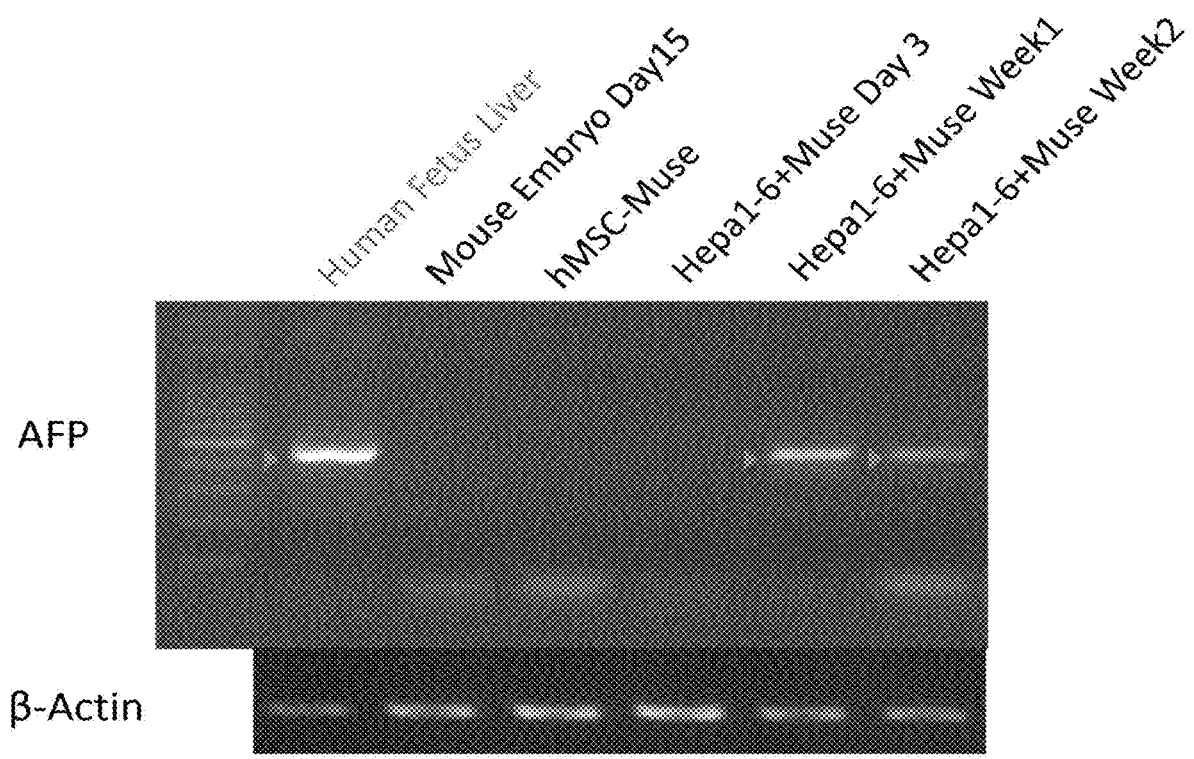
FIG. 10 illustrates the result of inducing differentiation into liver cells. It shows differentiation of Muse cells into liver cells, in which AFP is used as an indicator.

(5) Differentiation into Endodermal-Lineage Cells (Liver Cells) By using apoptotic liver cells (mouse liver cancer cell line: Hepa1-6) (ATCC, #CRL-1830), differentiation of Muse cells into endodermal cells was examined. Similar to the above experiment, etoposide treated apoptotic mouse liver cells were prepared and then co-cultured with Muse cells. From the Muse cells, total RNA was extracted at 3 days after and 1 to 2 week after starting the co-culture, and examined for Muse cell differentiation. More specifically, mRNA expression of α-fetoprotein (AFP), a marker for liver progenitor, was examined by RP-PCR. As it is illustrated in FIG. 10, expression of AFP was observed 1 week after starting the co-culture, and it was shown that, according to co-culture with damaged liver cells, differentiation of Muse cells into liver cells, which belong to endodermal-lineage cells, is yielded.

Furthermore, primers used for various markers as a detection subject in RT-PCR were designed and synthesized based on the nucleotide sequence of AFP (NM_001134; SEQ ID NO: 25). Specifically, they are described in the followings.

```
Forward primer:
                                            (SEQ ID NO: 26)
5'-CCGAACTTTCCAAGCCATAACTG-3'
(corresponding to 740-762 nt of SEQ ID NO: 25)

Reverse primer:
                                            (SEQ ID NO: 27)
5'-CACTTCTCCAATAACTCCTGGTATC-3'
(corresponding to 1195-1171 nt of SEQ ID NO: 25)
```

INDUSTRIAL APPLICABILITY

The present invention allows inducing differentiation of pluripotent stem cells, particularly Muse cells, into endodermal, mesodermal, and ectodermal-lineage cells by using the same method. The method can be applied to chronic diseases in which the "principle of the site" has been already lost. The method can also be applied to regeneration of avascular tissues and an organs where Muse cells cannot approach. The method can be applied to generation of rare cells. The method enables pluripotent stem cells such as Muse cells to stably provide a large scale of differentiated cells with easy approach and low cost. Such induced differentiated cells have low risks of tumorigenicity, different from cells that are induced to be differentiated by exogenous gene introduction, and thus can be applied to clinical treatment with low safety concerns.

All the publications and patent literature cited herein are incorporated into the present specification in their entirety as reference. The specific embodiments of the present invention were explained in the present specification for the purpose of example, and it will be easily appreciated by a person skilled in the art that various modifications may be employed such as are not outside of the spirit and scope of the present invention.

The invention claimed is:

1. A method for inducing differentiation of Multilineage-differentiating Stress Enduring (MUSE) cells as pluripotent stem cells in vitro into cells having the same phenotype and function as Information Presenting Cells for Differentiation (IPCD), the method comprising co-culturing the pluripotent stem cells or cell population with high content of the pluripotent stem cells either with damaged and/or dead cells as IPCD, and/or fragments of said damaged and/or dead cells,
wherein the pluripotent stem cells phagocytize the damaged and/or dead cells as IPCD, and/or fragments of said damaged and/or dead cells,
wherein the resulting differentiated cells exhibit characteristics of the IPCD,
the pluripotent stem cells are SSEA-3 positive and CD105-positive,
the pluripotent stem cells have all of the following properties:
(i) telomerase activity at low or under detection level;
(ii) having the ability to differentiate into cells of three germ layers;
(iii) exhibiting no tumorigenic proliferation; and
(iv) having self-renewal ability, and
the pluripotent stem cells are:
(v) CD117-negative and CD146-negative,
(vi) CD117-negative, CD146-negative, NG2-negative, CD34-negative, vWF-negative, and CD271-negative, or
(vii) CD34-negative, CD117-negative, CD146-negative, CD271-negative, NG2-negative, vWF-negative, Sox10-negative, Snail-negative, Slug-negative, Tyrp1-negative, and Dct-negative.

2. The method according to claim 1, wherein the pluripotent stem cells are isolated from mesenchymal tissues of a body or cultured mesenchymal cells.

3. The method according to claim 1, wherein the pluripotent stem cells are CD117-negative and CD146-negative.

4. The method according to claim 1, wherein the pluripotent stem cells are CD117-negative, CD146-negative, NG2-negative, CD34-negative, vWF-negative, and CD271-negative.

5. The method according to claim 1, wherein the pluripotent stem cells are CD34-negative, CD117-negative, CD146-negative, CD271-negative, NG2-negative, vWF-negative, Sox10-negative, Snail-negative, Slug-negative, Tyrp1-negative, and Dct-negative.

6. The method according to claim 1, wherein the ratio between the number of the pluripotent stem cells and the number of the damaged and/or dead cells as IPCD is in a range of 1:10,000 to 10,000:1.

7. The method according to claim 1, wherein the damaged and/or dead cells as IPCD, and/or fragments of said damaged and/or dead cells are obtained by adding a pharmaceutical agent selected from the group consisting of apoptosis inducing agent, metabolic antagonist, alkylating agent, anthracycline, antibiotics, antimitotic agent, topoisomerase inhibitor, proteasome inhibitor, anti-cancer agent, heat, low temperature, acid, alkali, ultrasonic wave, and physical disruption by vortex.

8. The method according to claim 1, wherein the IPCD are cells derived from ectoderm.

9. The method according to claim 8, wherein the cells derived from ectoderm are selected from the group consisting of neural cells, glial cells, pigment cells, skin cells, inner ear cells, retinal cells, corneal cells, and hair follicle cells.

10. The method according to claim 1, wherein the IPCD are cells derived from mesoderm.

11. The method according to claim 10, wherein the cells derived from mesoderm are selected from the group consisting of cardiac muscle cells, skeletal muscle cells, smooth muscle cells, osteocytes, chondrocytes, germ line cells, and hematopoietic cells.

12. The method according to claim 1, wherein the IPCD are cells derived from endoderm.

13. The method according to claim 12, wherein the cells derived from endoderm are selected from the group consisting of pancreatic β cells, liver cells, bile duct cells, respiratory epithelial cells, esophageal epithelial cell, vascular endothelial cells, kidney-constituting cells, bladder epithelial cells, and pancreatic exocrine cells.

14. The method according to claim 1, wherein the IPCD are selected from the group consisting of motor neuron, dopamine neuron, intermediate neuron, glutamine-activated neuron, pituitary gland cells, thyroid gland cells, adrenal cortex, adrenal medulla, pressure-sensor cells of carotid artery, heart conduction system, choroid plexus epithelial cells, pancreatic-alpha cells, pancreatic-delta cells, and lung Clara cells.

15. The method according to claim 1, wherein the co-culturing comprises co-culturing the pluripotent stem cells with neural cells.

16. The method according to claim 1, wherein the co-culturing comprises co-culturing the pluripotent stem cells with cardiac muscle cells or skeletal muscle cells.

17. The method according to claim 1, wherein the co-culturing comprises co-culturing the pluripotent stem cells with β cells or liver cells.

* * * * *